US007056512B1

(12) United States Patent
Klysner et al.

(10) Patent No.: US 7,056,512 B1
(45) Date of Patent: Jun. 6, 2006

(54) METHOD FOR DOWN-REGULATING GDF-8 ACTIVITY

(75) Inventors: Steen Klysner, Hillerod (DK); Soren Mouritsen, Birkerod (DK); Torben Halkier, Solrød Strand (DK)

(73) Assignee: Pharmexa A/S, Horsholm (DK)

( * ) Notice: Subject to any disclaimer, the term of this patent is extended or adjusted under 35 U.S.C. 154(b) by 1 day.

(21) Appl. No.: 09/620,586

(22) Filed: Jul. 20, 2000

Related U.S. Application Data

(60) Provisional application No. 60/145,275, filed on Jul. 26, 1999.

(30) Foreign Application Priority Data

Jul. 20, 1999 (DK) ............................... 1999 01014

(51) Int. Cl.
*A61K 39/00* (2006.01)
*A61K 39/38* (2006.01)

(52) U.S. Cl. ............................... 424/185.1; 424/192.1; 424/195.11; 424/184.1

(58) Field of Classification Search ............. 424/184.1, 424/185.1, 192.1, 195.11
See application file for complete search history.

(56) References Cited

U.S. PATENT DOCUMENTS

| | | | |
|---|---|---|---|
| 6,369,201 | B1 * | 4/2002 | Barker et al. |
| 6,607,884 | B1 | 8/2003 | Lee et al. |

FOREIGN PATENT DOCUMENTS

| | | | |
|---|---|---|---|
| GB | 2333706 | | 8/1999 |
| WO | WO 95/05849 | * | 3/1995 |
| WO | WO 95/07707 | | 3/1995 |
| WO | WO 98/23635 | | 6/1998 |
| WO | WO 98/46642 | | 10/1998 |
| WO | WO9902667 | | 1/1999 |
| WO | WO9942573 | | 8/1999 |

OTHER PUBLICATIONS

Colman et al., Research in Immunology 145(1):33-36, 1994.*

Abaza et al., Journal of Protein Chemistry 11(5):433-444, 1992.*

Lederman et al in Molecular Immunology 28:1171-1181, 1991.*

Van Regenmortel, A Comparion to Methods of Enzymology 9:465-472, 1996.*

Biochemistry 37 (16)(1998) 5709-19 Wearsch et al "Structural Transitions accompanying the activation of peptide binding".

Journal of Immunology 160 (1998) 3363-73 Southwood et al "Several common HLA-DR types share largely overlapping peptide binding repertoires".

Annu Rev Immunol 15 (1997) 617-48 Donnelly et al "DNA vaccines".

Life Sciences 60 (3) (1997) 163-72 Donnelly et al "Mini Review: DNA Vaccines".

Nature 387 (May 1, 1997) 83-89 McPherron et al Regulation of skeletal muscle mass in mice by a new TGF-β superfamily member.

Proc Natl Acad Sci USA 94 (Nov. 1997) 12457-61 McPherron et al "Double muscling in cattle due to mutations in the myostatin gene".

Immunology and Cell Biology 74 (1996) 8-25 Barr et al "ISCOMs (immunostimulating complexes): The first decade".

Journal of Immunology 157 (1996) 4796-4804 Dalum et al "Breaking of B cell tolerance toward a highly conserved self protein".

Science 271 (Jan. 19, 1996) 348-50 Dempsey et al "C3d of complement as a molecular adjuvant: bridging innate and acquired immunity".

Clin Immunother 3 (6) (1995) 461-75 Morein et al "Immunostimulating complexes".

La Revue du Praticien (Paris) 45 (1995) 1492-96 Saliou P "Les vaccins vivants".

Immunity 1 (9) (Dec. 1994) 751-61 Alexander et al Development of high potency universal DR-restricted helper epitopes by modification of high affinity DR-blocking peptides.

Immunogenetics 39 (1994) 230-42 Falk et al "Pool sequencing of natural HLA-DR, DQ, and DP ligands reveals detailed peptide motifs, constraints of . ."

(Continued)

*Primary Examiner*—Christina Chan
*Assistant Examiner*—Michail A. Belyavskyi
(74) *Attorney, Agent, or Firm*—Birch, Stewart, Kolasch & Birch, LLP.

(57) ABSTRACT

Disclosed are novel methods for increasing muscle mass by means of immunization against Growth Differentiation Factor 8 (GDF-8, myostatin). Immunization is preferably effected by administration of analogues of GDF-8 which are capable of inducing antibody production against homologous GDF-8. Especially preferred as an immunogen is homologous GDF-8 which has been modified by introduction of one single or a few foreign, immunodominant and promiscuous T-cell epitopes while substantially preserving the tertiary structure of the homologous GDF-8. Also disclosed are nucleic acid vaccination against GDF-8 and vaccination using live vaccines as well as methods and means useful for the vaccination. Such methods and means include methods for identification of useful immunogenic GDF-8 analogues, methods for the preparation of analogues and pharmaceutical formulations, as well as nucleic acid fragments, vectors, transformed cells, polypeptides and pharmaceutical formulations.

28 Claims, 5 Drawing Sheets

OTHER PUBLICATIONS

Figure 1A:
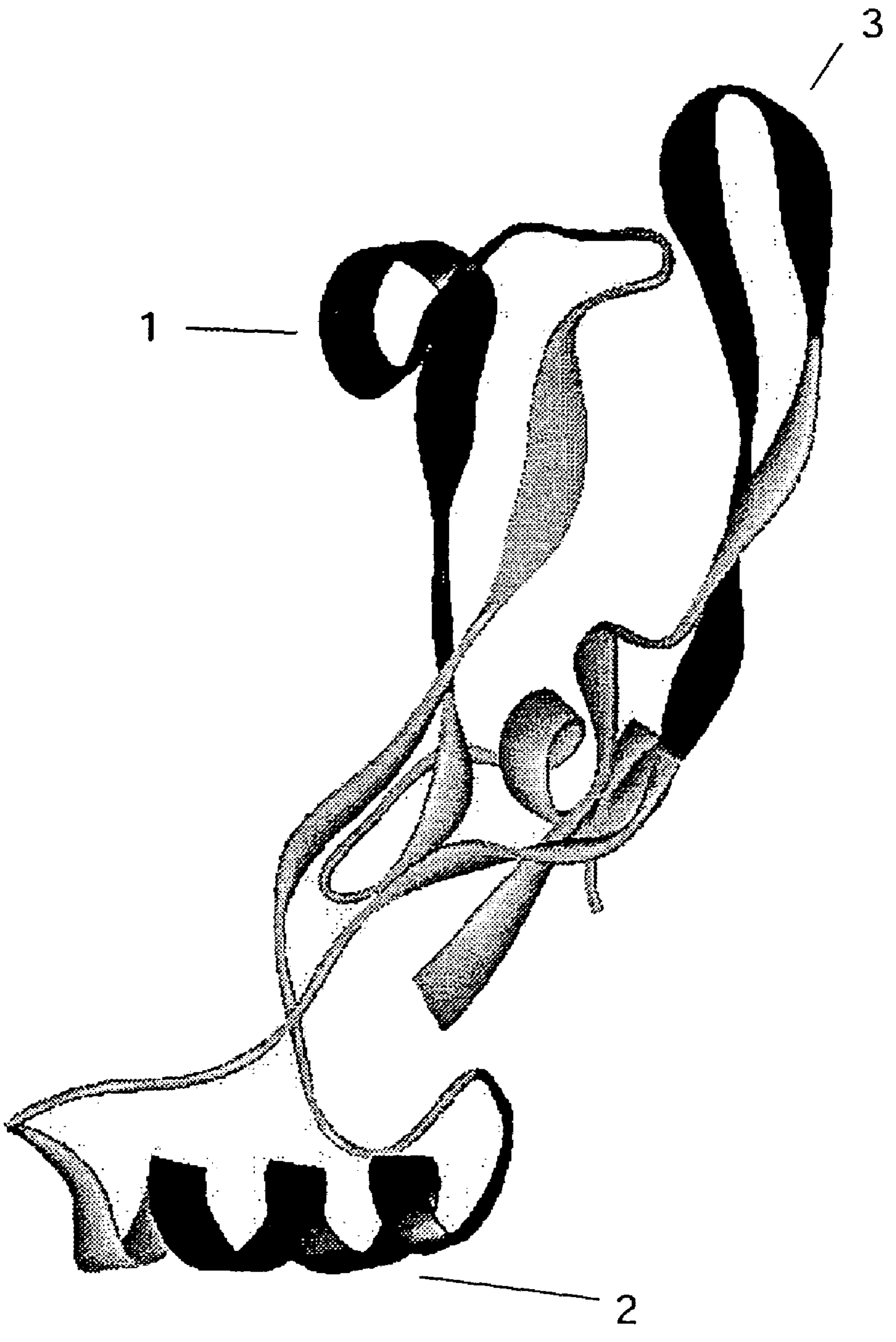
Figure 1B:
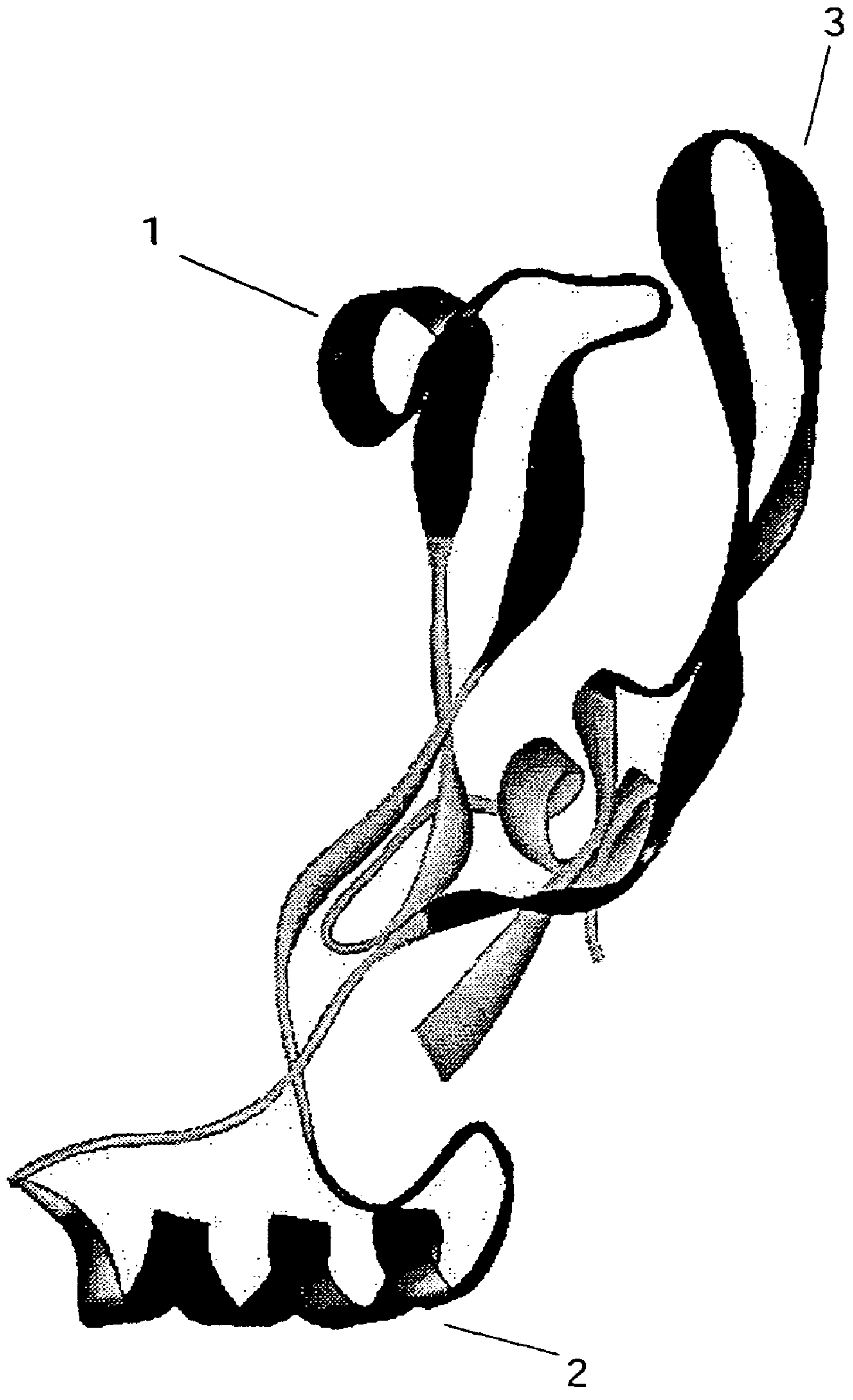
Figure 1C:
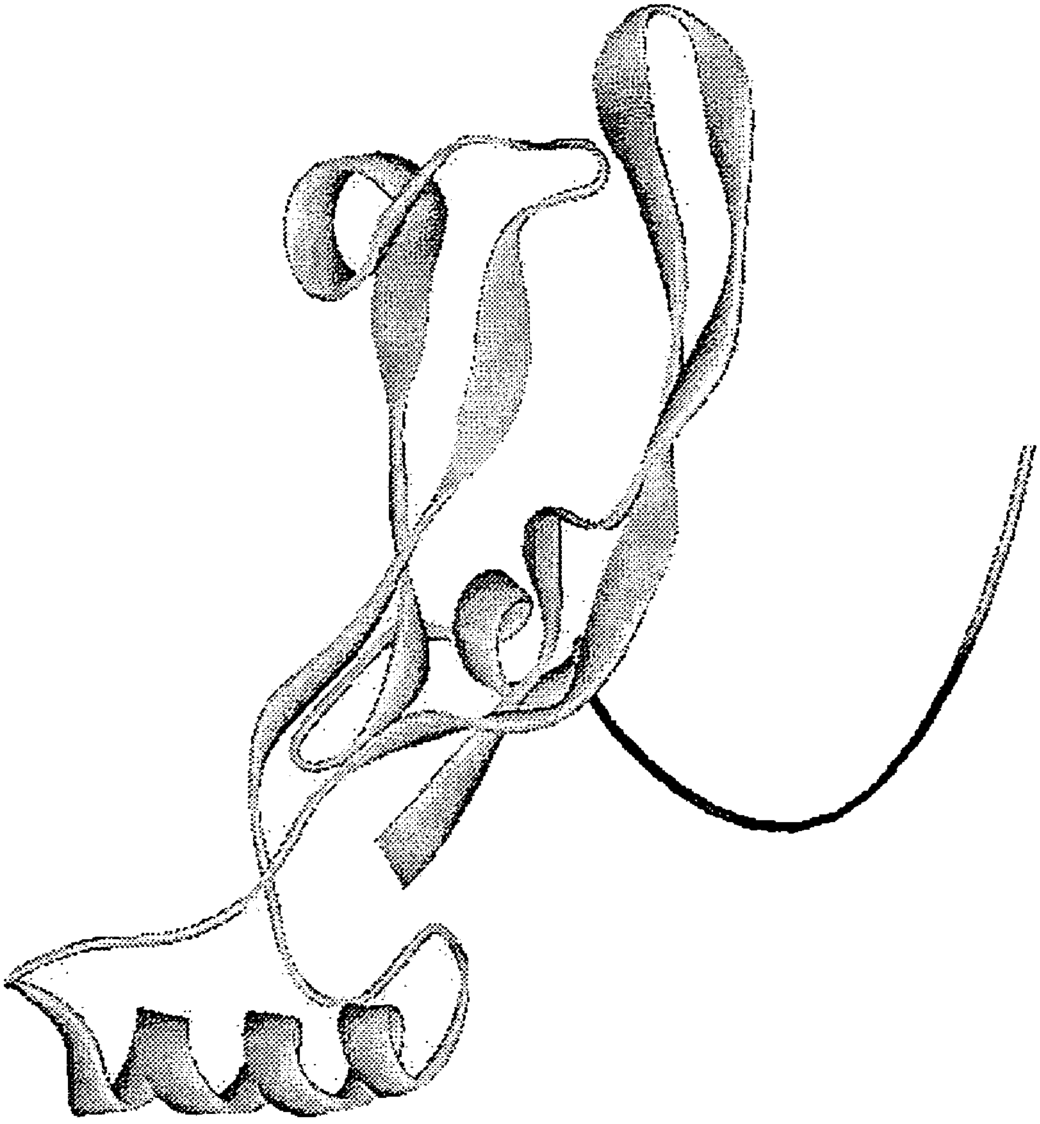
Figure 1D:
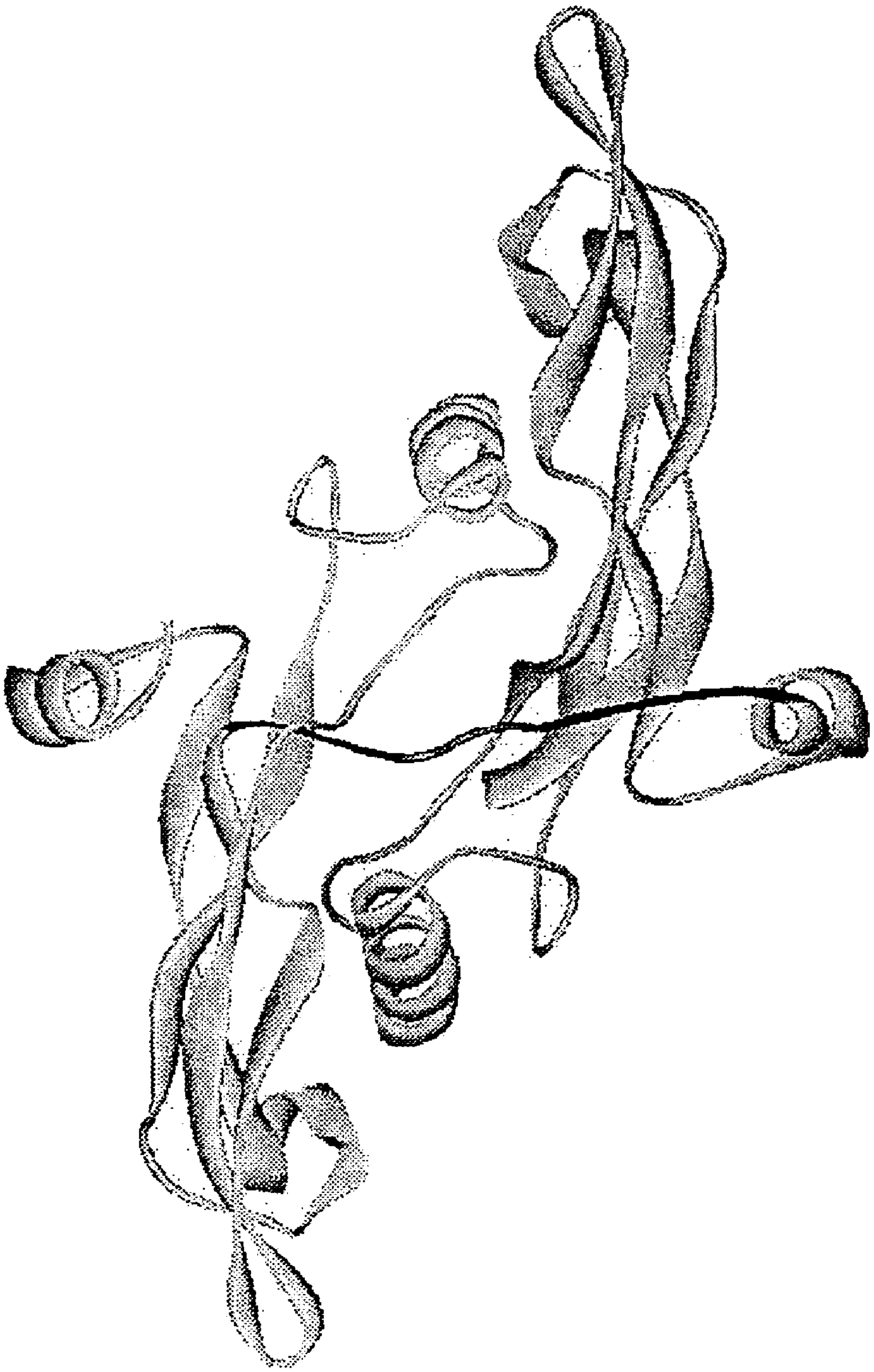

Cell 74 (Jul. 16, 1993) 197-203 Hammer et al Promiscuous and Allele-specific anchors in HLA-DR-binding peptides.
J Exp Med 178 (Jul. 1993) 27-47 Chicz et al "Specificity and promiscuity among naturally processed peptides bound to HLA-DR alleles".
J Immunol 149 (11) (Dec. 1, 1992) 3477-81 Gosselin et al "Enhanced antigen presentation using human Fc gamma receptor . .".
Vaccine 10 (14) (1992) 977-90 Walker PD "Bacterial vaccines: old and new, veterinary and medical".
Nature 336 (22/29) (Dec. 1988) 778-80 Sinigaglia et al "A malaria T cell epitope recognized in association with most mouse and human MHC class . .".
Bo Meng and Dahai Zhu, "Myostatin Regulates Skeletal Muscle Cell Differentiation in Chicken Primary Myoblast Cells", Molecular and Cellular Developmental Biology Laboratory Harbin Institute of Technology, Harbin, 150001.

* cited by examiner

METHOD FOR DOWN-REGULATING GDF-8 ACTIVITY

This application claims priority on provisional Application No. 60/145,275 filed on Jul. 26, 1999, the entire contents of which are hereby incorporated by reference, and Danish Application PA 1999 01014 filed on Jul. 20, 1999.

FIELD OF THE INVENTION

The present invention generally relates to the fields of animal and poultry husbandry as well as to human medicine. More specifically, the present invention pertains to improvements in controlling and increasing muscle growth, especially in farm animals for slaughter. Thus, provided are novel methods and means for increasing muscle growth in animals for slaughter.

BACKGROUND OF THE INVENTION

Currently, two different medical approaches are used in order to increase the growth rate of farm animals: On the one hand the administration to farm animals of antibiotics or antibiotic-like compounds, and on the other the administration of growth hormones.

The administration of antibiotics and antibiotic-like compounds in farm animals (notably pigs) in order to promote the growth rate of these animals has in later years been proven to cause several problems. Some of these compounds are chemically closely related to antibiotics used for treatment of human disease, and evidence is building up that extensive use of such compounds in farm animals induces cross-resistance towards human antibiotics in micro-organisms pathogenic in man. Further, relatively low increases in growth rates of 1–3% are obtained with these compounds.

The use of growth hormones in farm animals is expensive, and the treatment has to be repeated at rather short intervals due to the relatively short half-life of growth hormone. Furthermore, the presence of potential residual growth hormone in meat produced from treated animals has created some concerns in European consumers particularly.

GDF-8

GDF-8 or myostatin was discovered in May 1997 as a growth regulating factor selectively down-regulating skeletal muscle growth (McPherron et al., Nature, 387, 83–90, 1997). GDF-8 expression is restricted to the myotome compartment of developing embryonic somites, but it is also expressed in various muscle tissues throughout the body in the adult animal.

GDF-8 knock-out mice exhibit a strongly increased skeletal muscle mass. The increase in skeletal muscle mass appear to be widespread throughout the body, and isolated muscles from GDF-8 negative mice weigh about 2–3 times more than wild type muscles. The total body weights of the knock-out mice are about 35% higher than wild type mice and mice lacking the GDF-8 gene has more than 80% more muscle fibres compared to normal mice. The massive skeletal muscle enlargement observed in the knock-out mice is, however, not merely due to an increase in muscle fibre numbers but also to a significant muscle fibre hypertrophy. The cross-sectional muscle area of the GDF-8 knock-out mice is increased by about 14 to 49% depending on muscle type.

Interestingly, there is also observed an enhanced rate of muscle mass increase in adult transgenic mice compared to adult non-transgenic mice. Further, all GDF-8 negative mice has been shown to be viable and fertile.

In November 1997 the authors who originally discovered GDF-8 published that two breeds of cattle that are characterized by strongly increased muscle mass, Belgian Blue and Piedmontese, have mutations in the GDF-8 coding sequence and that this accounts for their large muscles (McPherron and Se-Jin Lee, 1997, PNAS 94, 12457–12461). This phenomenon of "double muscling" has been observed in many breeds of cattle for the past 190 years, and the animals have an average increase in muscle mass of 20–25%. They also show an increased feed efficiency, but they still produce high-quality meat.

Unlike the GDF-8 knock-out mice, however, the Belgian Blue cattle also exhibit a reduction in mass of most other organs. These "natural knock-out cows" also suffer from reduced female fertility, reduced viability of offspring, and a delayed sexual maturation.

The relative increase in muscle mass in "knock-out cows" is not nearly as pronounced as is observed in the knock-out mice—in fact, it corresponds to the extent of muscle hypertrophy observed in the mice. McPherron et al. speculate that one reason could be that normal cattle may be nearer than mice to a maximum limit of muscle size (and hence to the maximum obtainable number of muscle fibres) after generations of selective breeding. No data regarding the number of muscle fibre hyperplasia versus hypertrophy in cattle was published by the authors, but based on this assumption and the muscle hypertrophy observed in the knock-out mice, it could be possible that the increase in muscle mass and growth rate observed in e.g. the Belgian Blue cattle is largely due to muscle hypertrophy and to a lesser extent muscle hyperplasia.

Physiological Role of GDF-8

Expression of GDF-8 is highly restricted to skeletal muscle. There is a low level of expression in adipose tissue, but notably there is no expression in heart muscle. The physiological role of GDF-8 in the adult individual is not known, although it seems that GDF-8 may function as a specific negative regulator of skeletal muscle growth. Speculations about the physiological role centres upon important functions in exercise induced muscle hypertrophy or regeneration after muscle injury. GDF-8 may, however, also suppress adipose tissue growth. It is not known whether GDF-8 works locally or systemically during the growth of the animal.

Structure of GDF-8

GDF-8 belongs to the transforming growth factor β (TGF-β) super family which encompasses a group of structurally-related proteins involved in embryonic development. Human and bovine GDF-8 are produced as 375 amino acids long precursor proteins. As other TGF-β super family proteins GDF-8 is probably processed proteolytically into a much shorter C-terminal fragment of about 109 amino acids which form disulphide linked homodimers. The homodimer is probably the biologically active form of GDF-8.

The amino acid sequences of murine, rat, human, baboon, bovine, porcine, sheep, chicken and turkey GDF-8 are known and the GDF-8 molecule is highly conserved (McPherron and Se-Jin Lee, PNAS, 94, 12457–12461, 1997). The sequences of murine, rat, human, porcine, chicken and turkey GDF-8 are 100% identical in the C-terminal region, which probably contains the biologically active part of GDF-8. Both bovine and sheep GDF-8 only differ by two amino acid residues from human GDF-8 in the C-terminal region. Bovine GDF-8 has the sequence -Glu—

Gly- instead of -Lys-Glu- in positions 356–357, and sheep GDF-8 has two conservative substitutions (a Val in position 316 and an Arg in position 333 instead of Leu and Lys, respectively). None of the known GDF-8 proteins include potential N-glycosylation sites in their active C-terminal region.

OBJECT OF THE INVENTION

It is an object of the present invention to provide a recombinant therapeutic vaccine capable of effecting down-regulation of growth differentiation factor 8 (GDF-8) (also known as myostatin) in order to increase the muscle growth rate of farm animals. It is a further object to provide a method of vaccinating animals in order to increase the muscle growth rate. It is also an object to provide variants of GDF-8 which are capable of breaking autotolerance against autologous GDF-8. Yet a further object is to provide nucleic acid fragments, vectors and transformed cells which are all useful in the preparation of the vaccines and GDF-8 variants.

SUMMARY OF THE INVENTION

Based on the above-referenced findings in transgenic GDF-8 knock-out animals and in Belgian Blue and Piedmontese, the present inventors have developed the theory that it will be possible to down-regulate GDF-8 in animals by inducing an effective and fine-tuned immune response against GDF-8. Hence, what is basically provided by the present invention is a method and means to immunologically down-regulate GDF-8 in order to effect an increase the muscle mass in animals.

The advantages of this approach over known growth-enhancing measures in farm animals are several. First of all, problems relating to cross-resistance in pathological micro-organisms will not arise when using the present approach. Further, there will be no potential residual exogenously administered growth hormone in meat from animals which have been subjected to the present treatment. Finally, the ethical problems involved in the breeding and production of cattle like the Belgian Blue and the Piedmontese (where many calves are born by means of Caesarean section and where other organs are of reduced size) can be completely avoided by postponing the down-regulation of GDF-8 in the animals until after birth (e.g. in adult life only)—in fact, animals having an increased muscle mass need not give birth at all, and the treatment can therefore be reserved to those animals which are predestined to become slaughtered.

Since the number and type of muscle fibres is determined during embryonic life, it is not very likely that an anti-GDF-8 vaccine would increase the number of muscle fibres in adult farm animals. It is therefore neither certain nor likely that an anti-GDF-8 vaccine would be able to suppress GDF-8 to the same level as seen in GDF-8 knock-out animals. This would probably not be desirably either, since this perhaps could negatively affect meat quality, breeding capability, and fat ratio. Nevertheless, an increase in growth rate and/or maximum body weight of 5–25% obtained in vaccinated animals due to post partum muscle hypertrophy (a figure range which does not seem unrealistic) would still be interesting in the production of meat from cows, pigs and poultry.

The sequence identity of GDF-8 relative to other members of the TGF-β family is only 30–40 percent at the amino acid level. This low sequence identity will in all likelihood not create problems with cross-reactivity of antibodies induced towards GDF-8.

Thus, in its broadest and most general scope, the present invention relates to a method for in vivo down-regulation of growth differentiation factor 8 (GDF-8) activity in an animal, including a human being, the method comprising effecting presentation to the animal's immune system of an immunologically effective amount of

- at least one GDF-8 polypeptide or subsequence thereof which has been formulated so that immunization of the animal with the GDF-8 polypeptide or subsequence thereof induces production of antibodies against the GDF-8 polypeptide, and/or
- at least one GDF-8 analogue wherein is introduced at least one modification in the GDF-8 amino acid sequence which has as a result that immunization of the animal with the analogue induces production of antibodies against the GDF-8 polypeptide.

It is expected that 1–4 annual injections with an immunogenic composition according to the invention will be sufficient to obtain the desired effect, whereas administration of both growth hormones and antibiotics require much more frequent administrations to the animal in question.

The invention also relates to GDF-8 analogues as well as to nucleic acid fragments encoding a subset of these. Also immunogenic compositions comprising the analogues or the nucleic acid fragments are part of the invention.

The invention also relates to a method of identifying immunogenically effective analogues of GDF-8 as well as a method for preparing composition comprising the GDF-8 analogues.

LEGENDS TO THE FIGURES

FIG. 1: Models of GDF-8 derived autovaccine constructs. Stretches indicated in dark grey are the stretches in which substitutions with P2 and P30, respectively, are proposed to take place.

A: Monomer construct with P2 epitope inserts. "1" indicates a P2 substitution of amino acid residues 18–32 of the 109 aa C-terminal GDF-8 fragment, "2" indicates a P2 substitution of amino acid residues 52–66 of the 109 aa C-terminal GDF-8 fragment, and "3" indicates a P2 substitution of amino acid residues 83–97 of the 109 aa C-terminal GDF-8 fragment.

B: Monomer construct with P30 epitope inserts. "1" indicates a P30 substitution of amino acid residues 21–41 of the 109 aa C-terminal GDF-8 fragment, "2" indicates a P30 substitution of amino acid residues 49–69 of the 109 aa C-terminal GDF-8 fragment, and "3" indicates a P30 substitution of amino acid residues 79–99 or 84–104 of the 109 aa C-terminal GDF-8 fragment.

C: Extended monomer construct with P2 and P30 substituted into the 160 aa C-terminal GDF-8 fragment.

D: Dimer construct with the P2 and P30 epitopes serially linked between two copies of the 109 C-terminal GDF-8 fragment.

Figure 2:
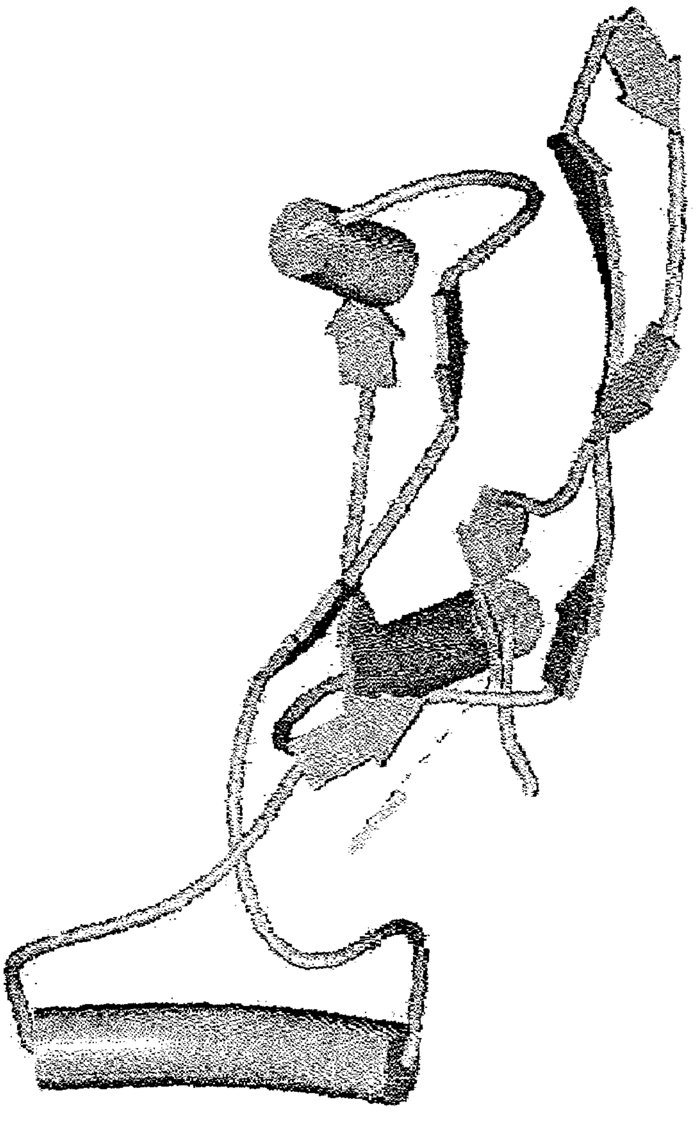

FIG. 2: Expected 3D structure of the TGF-β protein. The model is based on an analogous domain (TGJ-1) from the TGF-β protein. β-sheets are shown as arrows and helices as cylinders.

DETAILED DISCLOSURE OF THE INVENTION

Definitions

In the following, a number of terms used in the present specification and claims will be defined and explained in detail in order to clarify the metes and bounds of the invention.

The terms "T-lymphocyte" and "T-cell" will be used interchangeably for lymphocytes of thymic origin which are responsible for various cell mediated immune responses as well as for helper activity in the humoral immune response. Likewise, the terms "B-lymphocyte" and "B-cell" will be used interchangeably for antibody-producing lymphocytes.

A "GDF-8 polypeptide" is herein intended to denote polypeptides having the amino acid sequence of the above-discussed GDF-8 proteins derived from a number of animals (or truncates thereof sharing a substantial amount of B-cell epitopes with intact GDF-B), but also polypeptides having the amino acid sequence identical to xeno-analogues of these two proteins isolated from other species are embraced by the term. When using the term is normally meant the biologically active form, i.e. the C-terminal peptide which in humans is of 109 amino acids in length. Also unglycosylated forms of GDF-8 which are prepared in prokaryotic system are included within the boundaries of the term as are forms having varying O-glycosylation patterns due to the use of e.g. yeasts or other non-mammalian eukaryotic expression systems. It should, however, be noted that when using the term "a GDF-8 polypeptide" it is intended that the polypeptide in question is normally non-immunogenic when presented to the animal to be treated. In other words, the GDF-8 polypeptide is a self-protein or is a xeno-analogue of such a self-protein which will not normally give rise to an immune response against GDF-8 of the animal in question.

A "GDF-8 analogue" is a GDF-8 polypeptide which has been subjected to changes in its primary structure. Such a change can e.g. be in the form of fusion of a GDF-8 polypeptide to a suitable fusion partner (i.e. a change in primary structure exclusively involving C- and/or N-terminal additions of amino acid residues) and/or it can be in the form of insertions and/or deletions and/or substitutions in the GDF-8 polypeptide's amino acid sequence. Also derivatized GDF-8 molecules are encompassed by the term a "GDF-8 analogue", cf. the discussion below which deals with modifications of GDF-8.

It should be noted that the use as a vaccine in a human of e.g. a canine analogue of human GDF-8 can be imagined to produce the desired immunity against GDF-8. Such use of an xeno-analogue for immunization is also considered to be an "GDF-8 analogue" as defined above.

The term "polypeptide" is in the present context intended to mean both short peptides of from 2 to 10 amino acid residues, oligopeptides of from 11 to 100 amino acid residues, and polypeptides of more than 100 amino acid residues. Furthermore, the term is also intended to include proteins, i.e. functional biomolecules comprising at least one polypeptide; when comprising at least two polypeptides, these may form complexes, be covalently linked, or may be non-covalently linked. The polypeptide(s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring GDF-8 amino acid sequence or nucleic acid sequence, respectively.

The term "animal" is in the present context in general intended to denote an animal species (preferably mammalian), such as *Homo sapiens*, Canis domesticus, etc. and not just one single animal. However, the term also denotes a population of such an animal species, since it is important that the individuals immunized according to the method of the invention all harbour substantially the same GDF-8 allowing for immunization of the animals with the same immunogen(s). If, for instance, genetic variants of GDF-8 exist in a different population it may be necessary to use different immunogens in these different populations in order to be able to break the autotolerance towards GDF-8 in each population. It will be clear to the skilled person that an animal in the present context is a living being which has an immune system. It is preferred that the animal is a vertebrate, such as a mammal.

By the term "in vivo down-regulation of GDF-8 activity" is herein meant reduction in the living organism of the number of interactions between GDF-8 and its receptors (or between GDF-8 and other possible biologically important binding partners for this molecule). The down-regulation can be obtained by means of several mechanisms: Of these, simple interference with the active site in GDF-8 by antibody binding is the most simple. However, it is also within the scope of the present invention that the antibody binding results in removal of GDF-8 by scavenger cells (such as macrophages and other phagocytic cells).

The expression "effecting presentation . . . to the immune system" is intended to denote that the animal's immune system is subjected to an immunogenic challenge in a controlled manner. As will appear from the disclosure below, such challenge of the immune system can be effected in a number of ways of which the most important are vaccination with polypeptide containing "pharmaccines" (i.e. a vaccine which is administered to treat or ameliorate ongoing disease) or nucleic acid "pharmaccine" vaccination. The important result to achieve is that immune competent cells in the animal are confronted with the antigen in an immunologically effective manner, whereas the precise mode of achieving this result is of less importance to the inventive idea underlying the present invention.

The term "immunogenically effective amount" has its usual meaning in the art, i.e. an amount of an immunogen which is capable of inducing an immune response which significantly engages pathogenic agents which share immunological features with the immunogen.

When using the expression that the GDF-8 has been "modified" is herein meant a chemical modification of the polypeptide which constitutes the backbone of GDF-8. Such a modification can e.g. be derivatization (e.g. alkylation, acylation, esterification etc.) of certain amino acid residues in the GDF-8 sequence, but as will be appreciated from the disclosure below, the preferred modifications comprise changes of (or additions to) the primary structure of the GDF-8 amino acid sequence, i.e. modifications which results in the provision of a GDF-8 analogue where the primary amino acid sequence has been modified.

When discussing "autotolerance towards GDF-8" is understood that since GDF-8 is a self-protein in the population to be vaccinated, normal individuals in the population do not mount an immune response against GDF-8; it cannot be excluded, though, that occasional individuals in an animal population might be able to produce antibodies against native GDF-8, e.g. as part of an autoimmune disorder. At any rate, an animal will normally only be autotolerant towards its own GDF-8, but it cannot be excluded that GDF-8 analogues derived from other animal species or from a population having a different GDF-8 phenotype would also be tolerated by said animal.

A "foreign T-cell epitope" (or: "foreign T-lymphocyte epitope") is a peptide which is able to bind to an MHC molecule and which stimulates T-cells in an animal species. Preferred foreign T-cell epitopes in the invention are "promiscuous" epitopes, i.e. epitopes which bind to a substantial fraction of a particular class of MHC molecules in an animal species or population. Only a very limited number of such promiscuous T-cell epitopes are known, and they will be discussed in detail below. It should be noted that in order for the immunogens which are used according to the present invention to be effective in as large a fraction of an animal population as possible, it may be necessary to 1) insert several foreign T-cell epitopes in the same GDF-8 analogue or 2) prepare several GDF-8 analogues wherein each analogue has a different promiscuous epitope inserted. It should be noted also that the concept of foreign T-cell epitopes also encompasses use of cryptic T-cell epitopes, i.e. epitopes which are derived from a self-protein and which only exerts immunogenic behaviour when existing in isolated form without being part of the self-protein in question.

A "foreign T helper lymphocyte epitope" (a foreign $T_H$ epitope) is a foreign T cell epitope which binds an MHC Class II molecule and can be presented on the surface of an antigen presenting cell (APC) bound to the MHC Class II molecule.

A "functional part" of a (bio)molecule is in the present context intended to mean the part of the molecule which is responsible for at least one of the biochemical or physiological effects exerted by the molecule. It is well-known in the art that many enzymes and other effector molecules have an active site which is responsible for the effects exerted by the molecule in question. Other parts of the molecule may serve a stabilizing or solubility enhancing purpose and can therefore be left out if these purposes are not of relevance in the context of a certain embodiment of the present invention. For instance it is possible to use certain other cytokines as a modifying moiety in GDF-8 (cf. the detailed discussion below), and in such a case, the issue of stability may be irrelevant since the coupling to GDF-8 provides the stability necessary.

The term "adjuvant" has its usual meaning in the art of vaccine technology, i.e. a substance or a composition of matter which is 1) not in itself capable of mounting an immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is furthermore stronger than that induced by the immunogen alone.

"Targeting" of a molecule is in the present context intended to denote the situation where a molecule upon introduction in the animal will appear preferentially in certain tissue(s) or will be preferentially associated with certain cells or cell types. The effect can be accomplished in a number of ways including formulation of the molecule in composition facilitating targeting or by introduction in the molecule of groups which facilitates targeting. These issues will be discussed in detail below.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immuno-stimulating agent is an increased "alertness" of the immune system meaning that simultaneous or subsequent immunization with an immunogen induces a significantly more effective immune response compared to isolated use of the immunogen.

Preferred Embodiments of GDF-8 Activity Down-Regulation

It is preferred that the GDF-8 polypeptide used as an immunogen in the method of the invention is a modified molecule wherein at least one change is present in the GDF-8 amino acid sequence, since the chances of obtaining the all-important breaking of autotolerance towards GDF-8 is greatly facilitated that way. It should be noted that this does not exclude the possibility of using such a modified GDF-8 in formulations which further facilitate the breaking of autotolerance against GDF-8, e.g. formulations containing certain adjuvants discussed in detail below.

It has been shown (in Dalum I et al., 1996, J. Immunol. 157: 4796–4804) that potentially self-reactive B-lymphocytes recognizing self-proteins are physiologically present in normal individuals. However, in order for these B-lymphocytes to be induced to actually produce antibodies reactive with the relevant self-proteins, assistance is needed from cytokine producing T-helper lymphocytes ($T_H$-cells or $T_H$-lymphocytes). Normally this help is not provided because T-lymphocytes in general do not recognize T-cell epitopes derived from self-proteins when presented by antigen presenting cells (APCs). However, by providing an element of "foreignness" in a self-protein (i.e. by introducing an immunologically significant modification), T-cells recognizing the foreign element are activated upon recognizing the foreign epitope on an APC (such as, initially, a mononuclear cell). Polyclonal B-lymphocytes (which are also specialised APCs) capable of recognising self-epitopes on the modified self-protein also internalise the antigen and subsequently presents the foreign T-cell epitope(s) thereof, and the activated T-lymphocytes subsequently provide cytokine help to these self-reactive polyclonal B-lymphocytes. Since the antibodies produced by these polyclonal B-lymphocytes are reactive with different epitopes on the modified polypeptide, including those which are also present in the native polypeptide, an antibody cross-reactive with the non-modified self-protein is induced. In conclusion, the T-lymphocytes can be led to act as if the population of polyclonal B-lymphocytes have recognised an entirely foreign antigen, whereas in fact only the inserted epitope(s) is/are foreign to the host. In this way, antibodies capable of cross-reacting with non-modified self-antigens are induced.

Several ways of modifying a peptide self-antigen in order to obtain breaking of autotolerance are known in the art. Hence, according to the invention, the modification can include that

- at least one foreign T-cell epitope is introduced, and/or
- at least one first moiety is introduced which effects targeting of the modified molecule to an antigen presenting cell (APC), and/or
- at least one second moiety is introduced which stimulates the immune system, and/or
- at least one third moiety is introduced which optimises presentation of the modified GDF-8 polypeptide to the immune system.

However, all these modifications should be carried out while maintaining a substantial fraction of the original B-lymphocyte epitopes in active GDF-8, since the B-lymphocyte recognition of the native molecule is thereby enhanced.

In one preferred embodiment, side groups (in the form of foreign T-cell epitopes or the above-mentioned first, second and third moieties) are covalently or non-covalently introduced. This is intended to mean that stretches of amino acid residues derived from GDF-8 are derivatized without altering the primary amino acid sequence, or at least without introducing changes in the peptide bonds between the individual amino acids in the chain.

An alternative, and preferred, embodiment utilises amino acid substitution and/or deletion and/or insertion and/or addition (which may be effected by recombinant means or by means of peptide synthesis; modifications which involves longer stretches of amino acids can give rise to fusion polypeptides). One especially preferred version of this embodiment is the technique described in WO 95/05849, which discloses a method for down-regulating self-proteins by immunising with analogues of the self-proteins wherein a number of amino acid sequence(s) has been substituted with a corresponding number of amino acid sequence(s) which each comprise a foreign immunodominant T-cell epitope, while at the same time maintaining the overall tertiary structure of the self-protein in the analogue. For the purposes of the present invention, it is however sufficient if the modification (be it an amino acid insertion, addition, deletion or substitution) gives rise to a foreign T-cell epitope and at the same time preserves a substantial number of the B-cell epitopes in GDF-8. However, in order to obtain maximum efficacy of the immune response induced, it is preferred that the overall tertiary structure of GDF-8 is maintained in the modified molecule.

The following formula describes the GDF-8 constructs generally covered by the invention:

$$(MOD_1)_{s1}(GDF\text{-}8_{e1})_{n1}(MOD_2)_{s2}(GDF\text{-}8_{e2})_{n2} \ldots (MOD_x)_{sx}(GDF\text{-}8_{ex})_{nx} \quad (I)$$

where GDF-$8_{e1}$-GDF-$8_{ex}$ are x B-cell epitope containing subsequences of GDF-8 which independently are identical or non-identical and which may contain or not contain foreign side groups, x is an integer ≧3, n1-nx are x integers ≧0 (at least one is ≧1), $MOD_1$-$MOD_x$ are x modifications introduced between the preserved B-cell epitopes, and $s_1$-$s_x$ are x integers ≧0 (at least one is ≧1 if no side groups are introduced in the GDF-$8_e$ sequences). Thus, given the general functional restraints on the immunogenicity of the constructs, the invention allows for all kinds of permutations of the original GDF-8 sequence, and all kinds of modifications therein. Thus, included in the invention are modified GDF-8 obtained by omission of parts of the GDF-8 sequence which e.g. exhibit adverse effects in vivo or omission of parts which could give rise to undesired immunological reactions.

Maintenance of a substantial fraction of B-cell epitopes or even the overall tertiary structure of a protein which is subjected to modification as described herein can be achieved in several ways. One is simply to prepare a polyclonal antiserum directed against GDF-8 (e.g. an antiserum prepared in a rabbit) and thereafter use this antiserum as a test reagent (e.g. in a competitive ELISA) against the modified proteins which are produced. Modified versions (analogues) which react to the same extent with the antiserum as does GDF-8 must be regarded as having the same overall tertiary structure as GDF-8 whereas analogues exhibiting a limited (but still significant and specific) reactivity with such an antiserum are regarded as having maintained a substantial fraction of the original B-cell epitopes.

Alternatively, a selection of monoclonal antibodies reactive with distinct epitopes on GDF-8 can be prepared and used as a test panel. This approach has the advantage of allowing 1) an epitope mapping of GDF-8 and 2) a mapping of the epitopes which are maintained in the analogues prepared.

Of course, a third approach would be to resolve the 3-dimensional structure of GDF-8 or of a biologically active truncate thereof (cf. above) and compare this to the resolved three-dimensional structure of the analogues prepared. Three-dimensional structure can be resolved by the aid of X-ray diffraction studies and NMR-spectroscopy. Further information relating to the tertiary structure can to some extent be obtained from circular dichroism studies which have the advantage of merely requiring the polypeptide in pure form (whereas X-ray diffraction requires the provision of crystallized polypeptide and NMR requires the provision of isotopic variants of the polypeptide) in order to provide useful information about the tertiary structure of a given molecule. However, ultimately X-ray diffraction and/or NMR are necessary to obtain conclusive data since circular dichroism can only provide indirect evidence of correct 3-dimensional structure via information of secondary structure elements.

One preferred embodiment of the invention utilises multiple presentations of B-lymphocyte epitopes of GDF-8 (i.e. formula I wherein at least one B-cell epitope is present in two positions). This effect can be achieved in various ways, e.g. by simply preparing fusion polypeptides comprising the structure $(GDF\text{-}B)_m$, where m is an integer ≧2 and then introduce the modifications discussed herein in at least one of the GDF-8 sequences, or alternatively, inserted between at least two of the GDF-8 amino acid sequences. It is preferred that the modifications introduced includes at least one duplication of a B-lymphocyte epitope and/or the introduction of a hapten.

As mentioned above, the introduction of a foreign T-cell epitope can be accomplished by introduction of at least one amino acid insertion, addition, deletion, or substitution. Of course, the normal situation will be the introduction of more than one change in the amino acid sequence (e.g. insertion of or substitution by a complete T-cell epitope) but the important goal to reach is that the GDF-8 analogue, when processed by an antigen presenting cell (APC), will give rise to such a foreign immunodominant T-cell epitope being presented in context of an MCH Class II molecule on the surface of the APC. Thus, if the GDF-8 amino acid sequence in appropriate positions comprises a number of amino acid residues which can also be found in a foreign $T_H$ epitope then the introduction of a foreign $T_H$ epitope can be accomplished by providing the remaining amino acids of the foreign epitope by means of amino acid insertion, addition, deletion and substitution. In other words, it is not necessary to introduce a complete $T_H$ epitope by insertion or substitution.

It is preferred that the number of amino acid insertions, deletions, substitutions or additions is at least 2, such as 3, 4, 5, 6, 7, 8, 9, 10, 11, 12, 13, 14, 15, 16, 17, 18, 19, 20, and 25 insertions, substitutions, additions or deletions. It is furthermore preferred that the number of amino acid insertions, substitutions, additions or deletions is not in excess of 150, such as at most 100, at most 90, at most 80, and at most 70. It is especially preferred that the number of substitutions, insertions, deletions, or additions does not exceed 60, and in particular the number should not exceed 50 or even 40. Most preferred is a number of not more than 30. With respect to amino acid additions, it should be noted that these, when the resulting construct is in the form of a fusion polypeptide, is often considerably higher than 150.

Preferred embodiments of the invention include modification by introducing at least one foreign immunodominant $T_H$ epitope. It will be understood that the question of immune dominance of a $T_H$ epitope depends on the animal species in question. As used herein, the term "immunodominance" simply refers to epitopes which in the vaccinated individual gives rise to a significant immune response, but it is a well-known fact that a $T_H$ epitope which is immunodominant in one individual is not necessarily immunodominant in another individual of the same species, even though it may be capable of binding MHC-II molecules in the latter individual.

Another important point is the issue of MHC restriction of $T_H$ epitopes. In general, naturally occurring $T_H$ epitopes are MHC restricted, i.e. a certain peptide constituting a $T_H$ epitope will only bind effectively to a subset of MHC Class II molecules. This in turn has the effect that in most cases the use of one specific $T_H$ epitope will result in a vaccine component which is effective in a fraction of the population only, and depending on the size of that fraction, it can be necessary to include more $T_H$ epitopes in the same molecule, or alternatively prepare a multi-component vaccine wherein the components are GDF-8 variants which are distinguished from each other by the nature of the $T_H$ epitope introduced.

If the MHC restriction of the T-cells used is completely unknown (for instance in a situation where the vaccinated animal has a poorly defined MHC composition), the fraction of the animal population covered by a specific vaccine composition can be determined by means of the following formula:

$$f_{population} = 1 - \prod_{i=1}^{n} (1 - p_i) \qquad \text{(II)}$$

where $p_i$ is the frequency in the population of responders to the $i^{th}$ foreign T-cell epitope present in the vaccine composition, and n is the total number of foreign T-cell epitopes in the vaccine composition. Thus, a vaccine composition containing 3 foreign T-cell epitopes having response frequencies in the population of 0.8, 0.7, and 0.6, respectively, would give $$1-0.2\times 0.3\times 0.4=0.976$$

i.e. 97.6 percent of the population will statistically mount an MHC-II mediated response to the vaccine.

The above formula does not apply in situations where a more or less precise MHC restriction pattern of the peptides used is known. If, for instance a certain peptide only binds the human MHC-II molecules encoded by HLA-DR alleles DR1, DR3, DR5, and DR7, then the use of this peptide together with another peptide which binds the remaining MHC-II molecules encoded by HLA-DR alleles will accomplish 100% coverage in the population in question. Likewise, if the second peptide only binds DR3 and DR5, the addition of this peptide will not increase the coverage at all. If one bases the calculation of population response purely on MHC restriction of T-cell epitopes in the vaccine, the fraction of the population covered by a specific vaccine composition can be determined by means of the following formula:

$$f_{population} = 1 - \prod_{j=1}^{3} (1 - \varphi_j)^2 \qquad \text{(III)}$$

wherein $\phi_j$ is the sum of frequencies in the population of allelic haplotypes encoding MHC molecules which bind any one of the T-cell epitopes in the vaccine and which belong to the $j^{th}$ of the 3 known HLA loci (DP, DR and DQ); in practice, it is first determined which MHC molecules will recognize each T-cell epitope in the vaccine and thereafter these MHC molecules are listed by type (DP, DR and DQ)—then, the individual frequencies of the different listed allelic haplotypes are summed for each type, thereby yielding $\phi_1$, $\phi_2$, and $\phi_3$.

It may occur that the value pi in formula II exceeds the corresponding theoretical value $\pi_i$:

$$\pi_i = 1 - \prod_{j=1}^{3} (1 - v_j)^2 \qquad \text{(IV)}$$

wherein $v_j$ is the sum of frequencies in the population of allelic haplotypes encoding MHC molecules which bind the $i^{th}$ T-cell epitope in the vaccine and which belong to the $j^{th}$ of the 3 known HLA loci (DP, DR and DQ). This means that in $1-\pi_i$ of the population there is a frequency of responders of $f_{residual\_i}=(p_i-\pi_i)/(1-\pi_i)$. Therefore, formula III can be adjusted so as to yield formula V:

$$f_{population} = 1 - \prod_{j=1}^{3} (1 - \varphi_j)^2 + \left\{1 - \prod_{i=1}^{n} (1 - f_{\text{residual\_i}})\right\} \qquad \text{(V)}$$

where the term $1-f_{residual\_i}$ is set to zero if negative. It should be noted that formula V requires that all epitopes have been haplotype mapped against identical sets of haplotypes. Therefore, when selecting T-cell epitopes to be introduced in the IL5 analogue, it is important to include all knowledge of the epitopes which is available: 1) The frequency of responders in the population to each epitope, 2) MHC restriction data, and 3) frequency in the population of the relevant haplotypes.

There exists a number of naturally occurring "promiscuous" T-cell epitopes which are active in a large proportion of individuals of an animal species or an animal population and these are preferably introduced in the vaccine thereby reducing the need for a very large number of different GDF-8 analogues in the same vaccine.

The promiscuous epitope can according to the invention be a naturally occurring human T-cell epitope such as epitopes from tetanus toxoid (e.g. the P2 and P30 epitopes), diphtheria toxoid, Influenza virus hemagluttinin (HA), and *P. falciparum* CS antigen. Of course, when vaccinating other animals than humans care should be taken to utilise naturally occurring T-cell epitopes which are promiscuous in the animal in question.

Over the years a number of other promiscuous T-cell epitopes have been identified. Especially peptides capable of binding a large proportion of HLA-DR molecules encoded by the different HLA-DR alleles have been identified and these are all possible T-cell epitopes to be introduced in the GDF-8 analogues used according to the present invention. Cf. also the epitopes discussed in the following references which are hereby all incorporated by reference herein: WO 98/23635 (Frazer I H et al., assigned to The University of Queensland); Southwood S et. al, 1998, J. Immunol. 160: 3363–3373; Sinigaglia F et al., 1988, Nature 336: 778–780; Chicz R M et al., 1993, J. Exp. Med 178: 27–47; Hammer J et al., 1993, Cell 74: 197–203; and Falk K et al., 1994, Immunogenetics 39: 230–242. The latter reference also deals with HLA-DQ and -DP ligands. All epitopes listed in these 5 references are relevant as candidate natural epitopes to be used in the present invention, as are epitopes which share common motifs with these.

Alternatively, the epitope can be any artificial T-cell epitope which is capable of binding a large proportion of MHC Class II molecules. In this context the pan DR epitope peptides ("PADRE") described in WO 95/07707 and in the corresponding paper Alexander J et al., 1994, Immunity 1: 751–761 (both disclosures are incorporated by reference herein) are interesting candidates for epitopes to be used according to the present invention. It should be noted that the most effective PADRE peptides disclosed in these papers carry D-amino acids in the C- and N-termini in order to improve stability when administered. However, the present invention primarily aims at incorporating the relevant epitopes as part of the modified GDF-8 which should then subsequently be broken down enzymatically inside the lysosomal compartment of APCs to allow subsequent presentation in the context of an MHC-II molecule and therefore it is not expedient to incorporate D-amino acids in the epitopes used in the present invention.

One especially preferred PADRE peptide is the one having the amino acid sequence AKFVMWTLKAAA (SEQ ID NO. 24) or an immunologically effective subsequence thereof. This, and other epitopes having the same lack of MHC restriction are preferred T-cell epitopes which should be present in the GDF-8 analogues used in the inventive method. Such super-promiscuous epitopes will allow for the most simple embodiments of the invention wherein only one single modified GDF-8 is presented to the vaccinated animal's immune system.

As mentioned above, the modification of GDF-8 can also include the introduction of a first moiety which targets the modified GDF-8 to an APC or a B-lymphocyte. For instance, the first moiety can be a specific binding partner for a B-lymphocyte specific surface antigen or for an APC specific surface antigen. Many such specific surface antigens are known in the art. For instance, the moiety can be a carbohydrate for which there is a receptor on the B-lymphocyte or on the APC (e.g. mannan or mannose). Alternatively, the second moiety can be a hapten. Also an antibody fragment which specifically recognizes a surface molecule on APCs or lymphocytes can be used as a first moiety (the surface molecule can e.g. be an FC receptor of macrophages and monocytes, such as FC RI or, alternatively any other specific surface marker such as CD40 or CTLA-4). It should be noted that all these exemplary targeting molecules can be used as part of an adjuvant also, cf. below.

As an alternative or supplement to targeting the modified GDF-8 polypeptide to a certain cell type in order to achieve an enhanced immune response, it is possible to increase the level of responsiveness of the immune system by including the above-mentioned second moiety which stimulates the immune system. Typical examples of such second moieties are cytokines, and heat-shock proteins, as well as effective parts thereof.

Suitable cytokines to be used according to the invention are those which will normally also function as adjuvants in a vaccine composition, i.e. for instance interferon γ (IFN-γ), Flt3L, interleukin 1 (IL-1), interleukin 2 (IL-2), interleukin 4 (IL-4), interleukin 6 (IL-6), interleukin 12 (IL-12), interleukin 13 (IL-13), interleukin 15 (IL-15), and granulocyte-macrophage colony stimulating factor (GM-CSF); alternatively, the functional part of the cytokine molecule may suffice as the second moiety. With respect to the use of such cytokines as adjuvant substances, cf. the discussion below.

According to the invention, suitable heat shock proteins used as the second moiety can be HSP70, HSP90, HSC70, GRP94 (also known as gp96, cf. Wearsch P A et al. 1998, Biochemistry 37: 5709–19), and CRT (calreticulin).

Alternatively, the second moiety can be a toxin, such as listeriolycin (LLO), lipid A and heat-labile enterotoxin. Also, a number of mycobacterial derivatives such as MDP (muramyl dipeptide) and the trehalose diesters TDM and TDE are interesting possibilities.

Also the possibility of introducing a third moiety which enhances the presentation of the modified GDF-8 to the immune system is an important embodiment of the invention. The art has shown several examples of this principle. For instance, it is known that the palmitoyl lipidation anchor in the *Borrelia burgdorferi* protein OspA can be utilised so as to provide self-adjuvating polypeptides (cf. e.g. WO 96/40718). It seems that the lipidated proteins form up micelle-like structures with a core consisting of the lipidation anchor parts of the polypeptides and the remaining parts of the molecule protruding therefrom, resulting in multiple presentations of the antigenic determinants. Hence, the use of this and related approaches using different lipidation anchors (e.g. a myristyl group, a myristyl group, a farnesyl group, a geranyl—geranyl group, a GPI-anchor, and an N-acyl diglyceride group) are preferred embodiments of the invention, especially since the provision of such a lipidation anchor in a recombinantly produced protein is fairly straightforward and merely requires use of e.g. a naturally occurring signal sequence as a fusion partner for the modified GDF-8 polypeptide. Another possibility is use of the C3d fragment of complement factor C3 or C3 itself (cf. Dempsey et al., 1996, Science 271, 348–350 and Lou & Kohler, 1998, Nature Biotechnology 16, 458–462).

An alternative embodiment of the invention which also results in the preferred presentation of multiple (e.g. at least 2) copies of the important epitopic regions of GDF-8 to the immune system is the covalent or non-covalent coupling of GDF-8, subsequence or variants thereof to certain carrier molecules. For instance, polymers can be used, e.g. carbohydrates such as dextran, cf. e.g. Lees A et al., 1994, Vaccine 12: 1160–1166; Lees A et al., 1990, J. Immunol. 145: 3594–3600, but also mannose and mannan are useful alternatives. Integral membrane proteins from e.g. *E. coli* and other bacteria are also useful conjugation partners. The traditional carrier molecules such as keyhole limpet hemocyanin (KLH), tetanus toxoid, diphtheria toxoid, and bovine serum albumin (BSA) are also preferred and useful conjugation partners.

Certain areas of native GDF-8 are believed to be superiorly suited for performing modifications. It is predicted that modifications in at least one of the following subsequences of C-terminal GDF-8 will result in suitable immunogenic molecules: Residues 18–41, 49–69, or 79–104 in SEQ ID NO: 11 or 12, or corresponding subsequences from GDF-8 polypeptides of different origin than human, bovine, porcine, chicken or turkey. Considerations underlying these chosen areas are a) preservation of B-cell epitopes, b) preservation of secondary, tertiary and quaternary structures etc. At any rate, as discussed herein, it is fairly easy to screen a set of modified GDF-8 molecules (which have all been subjected to introduction of a T-cell epitope in different locations) for immune reactivity with antibodies raised against a native GDF-8. It is especially preferred that the modification is performed by substituting an amino acid sequence with at least one amino acid sequence of equal or different length which contains a foreign $T_H$ epitope. The rationale behind such constructs is discussed in detail in the examples. Also insertion (or substitution) into any one of the loop areas or the flexible termini (residues 1–12, 18–30, 42–51, 82–86, and 105–109) of the C-terminal GDF-8 fragment is preferred.

Formulation of GDF-8 and Modified GDF-8 Polypeptides

When effecting presentation of the GDF-8 polypeptide or the modified GDF-8 polypeptide to an animal's immune system by means of administration thereof to the animal, the formulation of the polypeptide follows the principles generally acknowledged in the art.

Preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines; cf. the detailed discussion of adjuvants below.

The vaccines are conventionally administered parenterally, by injection, for example, either subcutaneously, intracutaneously, intradermally, subdermally or intramuscularly. Additional formulations which are suitable for other modes of administration include suppositories and, in some cases, oral, buccal, sublingual, intraperitoneal, intravaginal, anal, epidural, spinal, and intracranial formulations. For suppositories, traditional binders and carriers may include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredient, preferably 25–70%. For oral formulations, cholera toxin is an interesting formulation partner (and also a possible conjugation partner).

The polypeptides may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 2000 μg (even though higher amounts in the 1–10 mg range are contemplated), such as in the range from about 0.5 μg to 1000 μg, preferably in the range from 1 μg to 500 μg and especially in the range from about 10 μg to 100 μg. Suitable regimens for initial administration and booster shots are also variable but are typified by an initial administration followed by subsequent inoculations or other administrations.

The manner of application may be varied widely. Any of the conventional methods for administration of a vaccine are applicable. These include oral application on a solid physiologically acceptable base or in a physiologically acceptable dispersion, parenterally, by injection or the like. The dosage of the vaccine will depend on the route of administration and will vary according to the age of the person to be vaccinated and the formulation of the antigen.

Some of the polypeptides of the vaccine are sufficiently immunogenic in a vaccine, but for some of the others the immune response will be enhanced if the vaccine further comprises an adjuvant substance.

Various methods of achieving adjuvant effect for the vaccine are known. General principles and methods are detailed in "The Theory and Practical Application of Adjuvants", 1995, Duncan E. S. Stewart-Tull (ed.), John Wiley & Sons Ltd, ISBN 0-471 -95170-6, and also in "Vaccines: New Generation Immunological Adjuvants", 1995, Gregoriadis G et al. (eds.), Plenum Press, New York, ISBN 0-306-45283-9, both of which are hereby incorporated by reference herein.

It is especially preferred to use an adjuvant which can be demonstrated to facilitate breaking of the autotolerance to autoantigens; in fact, this is essential in cases where unmodified GDF-8 is used as the active ingredient in the autovaccine. Non-limiting examples of suitable adjuvants are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM matrix); a particle; DDA; aluminium adjuvants; DNA adjuvants; γ-inulin; and an encapsulating adjuvant. In general it should be noted that the disclosures above which relate to compounds and agents useful as first, second and third moieties in the analogues also refer mutatis mutandis to their use in the adjuvant of a vaccine of the invention.

The application of adjuvants include use of agents such as aluminium hydroxide or phosphate (alum), commonly used as 0.05 to 0.1 percent solution in buffered saline, admixture with synthetic polymers of sugars (e.g. Carbopol®) used as 0.25 percent solution, aggregation of the protein in the vaccine by heat treatment with temperatures ranging between 70 to 101° C. for 30 second to 2 minute periods respectively and also aggregation by means of cross-linking agents are possible. Aggregation by reactivation with pepsin treated antibodies (Fab fragments) to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Admixture with oils such as squalene and IFA is also preferred.

According to the invention DDA (dimethyldioctadecylammonium bromide) is an interesting candidate for an adjuvant as is DNA and γ-inulin, but also Freund's complete and incomplete adjuvants as well as quillaja saponins such as QuilA and QS21 are interesting as is RIBI. Further possibilities are monophosphoryl lipid A (MPL), the above mentioned C3 and C3d, and muramyl dipeptide (MDP).

Liposome formulations are also known to confer adjuvant effects, and therefore liposome adjuvants are preferred according to the invention.

Also immunostimulating complex matrix type (ISCOM® matrix) adjuvants are preferred choices according to the invention, especially since it has been shown that this type of adjuvants are capable of up-regulating MHC Class II expression by APCs. An ISCOM® matrix consists of (optionally fractionated) saponins (triterpenoids) from Quillaja saponaria, cholesterol, and phospholipid. When admixed with the immunogenic protein, the resulting particulate formulation is what is known as an ISCOM particle where the saponin constitutes 60–70% w/w, the cholesterol and phospholipid 10–15% w/w, and the protein 10–15% w/w. Details relating to composition and use of immunostimulating complexes can e.g. be found in the above-mentioned text-books dealing with adjuvants, but also Morein B et al., 1995, Clin. Immunother. 3: 461–475 as well as Barr I G and Mitchell G F, 1996, Immunol. and Cell Biol. 74: 8–25 (both incorporated by reference herein) provide useful instructions for the preparation of complete immunostimulating complexes.

Another highly interesting (and thus, preferred) possibility of achieving adjuvant effect is to employ the technique described in Gosselin et al., 1992 (which is hereby incorporated by reference herein). In brief, the presentation of a relevant antigen such as an antigen of the present invention can be enhanced by conjugating the antigen to antibodies (or antigen binding antibody fragments) against the Fcγ receptors on monocytes/macrophages. Especially conjugates between antigen and anti-FcγRI have been demonstrated to enhance immunogenicity for the purposes of vaccination.

Other possibilities involve the use of the targeting and immune modulating substances (i.a. cytokines) mentioned above as candidates for the first and second moieties in the modified versions of GDF-8. In this connection, also synthetic inducers of cytokines like poly I:C are possibilities.

Suitable mycobacterial derivatives are selected from the group consisting of muramyl dipeptide, complete Freund's adjuvant, RIBI, and a diester of trehalose such as TDM and TDE.

Suitable immune targeting adjuvants are selected from the group consisting of CD40 ligand and CD40 antibodies or specifically binding fragments thereof (cf. the discussion above), mannose, a Fab fragment, and CTLA-4.

Suitable polymer adjuvants are selected from the group consisting of a carbohydrate such as dextran, PEG, starch, mannan, and mannose; a plastic polymer such as; and latex such as latex beads.

Yet another interesting way of modulating an immune response is to include the GDF-8 immunogen (optionally together with adjuvants and pharmaceutically acceptable carriers and vehicles) in a "virtual lymph node" (VLN) (a proprietary medical device developed by ImmunoTherapy, Inc., 360 Lexington Avenue, New York, N.Y. 10017-6501). The VLN (a thin tubular device) mimics the structure and function of a lymph node. Insertion of a VLN under the skin creates a site of sterile inflammation with an upsurge of cytokines and chemokines. T- and B-cells as well as APCs rapidly respond to the danger signals, home to the inflamed site and accumulate inside the porous matrix of the VLN. It has been shown that the necessary antigen dose required to mount an immune response to an antigen is reduced when using the VLN and that immune protection conferred by vaccination using a VLN surpassed conventional immunization using Ribi as an adjuvant. The technology is i.a. described briefly in Gelber C et al., 1998, "Elicitation of Robust Cellular and Humoral Immune Responses to Small Amounts of Immunogens Using a Novel Medical Device Designated the Virtual Lymph Node", in: "From the Laboratory to the Clinic, Book of Abstracts, Oct. $12^{th}$–$15^{th}$ 1998, Seascape Resort, Aptos, California".

It is expected that the vaccine should be administered at least once a year, such as at least 1, 2, 3, 4, 5, 6, and 12 times a year. More specifically, 1–12 times per year is expected, such as 1, 2, 3, 4, 5, 6, 7, 8, 9, 10, 11, or 12 times a year to an individual in need thereof. It has previously been shown that the memory immunity induced by the use of the preferred autovaccines according to the invention is not permanent, and therefore the immune system needs to be periodically challenged with the analogues.

Due to genetic variation, different individuals may react with immune responses of varying strength to the same polypeptide. Therefore, the vaccine according to the invention may comprise several different polypeptides in order to increase the immune response, cf. also the discussion above concerning the choice of foreign T-cell epitope introductions. The vaccine may comprise two or more polypeptides, where all of the polypeptides are as defined above.

The vaccine may consequently comprise 3–20 different modified or unmodified polypeptides, such as 3–10 different polypeptides. However, normally the number of polypeptides will be sought kept to a minimum such as 1 or 2 polypeptides.

Nucleic Acid Vaccination

As an alternative to classic administration of a peptide-based vaccine, the technology of nucleic acid vaccination (also known as "nucleic acid immunisation", "genetic immunisation", and "gene immunisation") offers a number of attractive features.

First, in contrast to the traditional vaccine approach, nucleic acid vaccination does not require resource consuming large-scale production of the immunogenic agent (e.g. in the form of industrial scale fermentation of micro-organisms producing modified GDF-8). Furthermore, there is no need to device purification and refolding schemes for the immunogen. And finally, since nucleic acid vaccination relies on the biochemical apparatus of the vaccinated individual in order to produce the expression product of the nucleic acid introduced, the optimum posttranslational processing of the expression product is expected to occur; this is especially important in the case of autovaccination, since, as mentioned above, a significant fraction of the original GDF-8 B-cell epitopes should be preserved in the modified molecule, and since B-cell epitopes in principle can be constituted by parts of any (bio)molecule (e.g. carbohydrate, lipid, protein etc.). Therefore, native glycosylation and lipidation patterns of the immunogen may very well be of importance for the overall immunogenicity and this is expected to be ensured by having the host producing the immunogen.

Hence, a preferred embodiment of the invention comprises effecting presentation of modified GDF-8 to the immune system by introducing nucleic acid(s) encoding the modified GDF-8 into the animal's cells and thereby obtaining in vivo expression by the cells of the nucleic acid(s) introduced.

In this embodiment, the introduced nucleic acid is preferably DNA which can be in the form of naked DNA, DNA formulated with charged or uncharged lipids, DNA formulated in liposomes, DNA included in a viral vector, DNA formulated with a transfection-facilitating protein or polypeptide, DNA formulated with a targeting protein or polypeptide, DNA formulated with Calcium precipitating agents, DNA coupled to an inert carrier molecule, and DNA formulated with an adjuvant. In this context it is noted that practically all considerations pertaining to the use of adjuvants in traditional vaccine formulation apply for the formulation of DNA vaccines. Hence, all disclosures herein which relate to use of adjuvants in the context of polypeptide based vaccines apply mutatis mutandis to their use in nucleic acid vaccination technology.

As for routes of administration and administration schemes of polypeptide based vaccines which have been detailed above, these are also applicable for the nucleic acid vaccines of the invention and all discussions above pertaining to routes of administration and administration schemes for polypeptides apply mutatis mutandis to nucleic acids. To this should be added that nucleic acid vaccines can suitably be administered intravenously and intraarterially. Furthermore, it is well-known in the art that nucleic acid vaccines can be administered by use of a so-called gene gun, and hence also this and equivalent modes of administration are regarded as part of the present invention. Finally, also the use of a VLN in the administration of nucleic acids has been reported to yield good results, and therefore this particular mode of administration is particularly preferred.

Furthermore, the nucleic acid(s) used as an immunization agent can contain regions encoding the $1^{st}$, $2^{nd}$ and/or $3^{rd}$ moieties, e.g. in the form of the immunomodulating substances described above such as the cytokines discussed as useful adjuvants. A preferred version of this embodiment encompasses having the coding region for the analogue and the coding region for the immunomodulator in different reading frames or at least under the control of different promoters. Thereby it is avoided that the analogue or epitope is produced as a fusion partner to the immunomodulator. Alternatively, two distinct nucleotide fragments can be used, but this is less preferred because of the advantage of ensured co-expression when having both coding regions included in the same molecule.

Accordingly, the invention also relates to a composition for inducing production of antibodies against GDF-8, the composition comprising

- a nucleic acid fragment or a vector of the invention (cf. the discussion of vectors below), and
- a pharmaceutically and immunologically acceptable vehicle and/or carrier and/or adjuvant as discussed above.

Under normal circumstances, the GDF-8 variant-encoding nucleic acid is introduced in the form of a vector wherein expression is under control of a viral promoter. For more detailed discussions of vectors and DNA fragments according to the invention, cf. the discussion below. Also, detailed disclosures relating to the formulation and use of nucleic acid vaccines are available, cf. Donnelly JJ et al., 1997, Annu. Rev. Immunol. 15: 617–648 and Donnelly JJ et al., 1997, Life Sciences 60: 163–172. Both of these references are incorporated by reference herein.

Live Vaccines

A third alternative for effecting presentation of modified GDF-8 to the immune system is the use of live vaccine technology. In live vaccination, presentation to the immune system is effected by administering, to the animal, a non-pathogenic micro-organism which has been transformed with a nucleic acid fragment encoding a modified GDF-8 or with a vector incorporating such a nucleic acid fragment. The non-pathogenic microorganism can be any suitable attenuated bacterial strain (attenuated by means of passaging or by means of removal of pathogenic expression products by recombinant DNA technology), e.g. *Mycobacterium bovis* BCG., non-pathogenic *Streptococcus* spp., *E. coli, Salmonella* spp., *Vibrio cholerae, Shigella*, etc. Reviews dealing with preparation of state-of-the-art live vaccines can e.g. be found in Saliou P, 1995, Rev. Prat. 45: 1492–1496 and Walker PD, 1992, Vaccine 10: 977–990, both incorporated by reference herein. For details about the nucleic acid fragments and vectors used in such live vaccines, cf. the discussion below.

As an alternative to bacterial live vaccines, the nucleic acid fragment of the invention discussed below can be incorporated in a non-virulent viral vaccine vector such as a vaccinia strain or any other suitable pox virus which will be infectious in the animal to be vaccinated.

Normally, the non-pathogenic micro-organism or virus is administered only once to the animal, but in certain cases it may be necessary to administer the micro-organism more than once in a lifetime in order to maintain protective immunity. It is even contemplated that immunization schemes as those detailed above for polypeptide vaccination will be useful when using live or virus vaccines.

Alternatively, live or virus vaccination is combined with previous or subsequent polypeptide and/or nucleic acid vaccination. For instance, it is possible to effect primary immunization with a live or virus vaccine followed by subsequent booster immunizations using the polypeptide or nucleic acid approach.

The micro-organism or virus can be transformed with nucleic acid(s) containing regions encoding the $1^{st}$, $2^{nd}$ and/or $3^{rd}$ moieties, e.g. in the form of the immunomodulating substances described above such as the cytokines discussed as useful adjuvants. A preferred version of this embodiment encompasses having the coding region for the analogue and the coding region for the immunomodulator in different reading frames or at least under the control of different promoters. Thereby it is avoided that the analogue or epitopes are produced as fusion partners to the immunomodulator. Alternatively, two distinct nucleotide fragments can be used as transforming agents. Of course, having the $1^{st}$ and/or $2^{nd}$ and/or $3^{rd}$ moieties in the same reading frame can provide as an expression product, an analogue of the invention, and such an embodiment is especially preferred according to the present invention.

Use of the Method of the Invention in Meat Production and in Disease Treatment

As will be appreciated from the discussions above, the provision of the method of the invention for down-regulation of GDF-8 activity allows for stimulation of the growth of skeletal muscle mass in animals. Hence, an important embodiment of the method of the invention for down-regulating GDF-8 activity comprises increasing the skeletal muscle mass of an animal, the method comprising down-regulating GDF-8 activity according to the method of the invention to such an extent that the muscle mass is statistically significantly increased (at a confidence level of 95%) and with at least 5%, when compared to control animals exhibiting a normal GDF-8 activity.

The increase in muscle mass may preferably be higher, such as at least 10, 15, 20, 25, 30, 35, 40, or even 45%, cf. the increases in muscle mass which have been observed in transgenic mice and naturally occurring GDF-8 deficient animals.

The muscle mass can be determined by any convenient method known in the art for assessing total and/or relative muscle mass.

An anti-GDF-8 vaccine could potentially also be useful for treatment of certain human diseases such as cancer cachexia, where muscular atrophy is a pronounced phenomenon, and it is also a feasible means of treatment/amelioration in other atrophic muscular diseases. Recent reports also suggest that suppression of GDF-8 would be beneficial in patients suffering from acute and chronic heart failure.

Peptides, Polypeptides, and Compositions of the Invention

As will be apparent from the above, the present invention is based on the concept of immunising individuals against the GDF-8 antigen in order to obtain an increase in muscle growth rate. The preferred way of obtaining such an immunization is to use modified versions of GDF-8, thereby providing molecules which have not previously been disclosed in the art.

It is believed that the modified GDF-8 molecules discussed herein are inventive in their own right, and therefore an important part of the invention pertains to a GDF-8 analogue which is derived from an animal GDF-8 wherein is introduced a modification which has as a result that immunization of the animal with the analogue induces production of antibodies reacting specifically with the unmodified GDF-8 polypeptide. Preferably, the nature of the modification conforms with the types of modifications described above when discussing various embodiments of the method of the invention when using modified GDF-8. Hence, any disclosure presented herein pertaining to modified GDF-8 molecules are relevant for the purpose of describing the GDF-8 analogues of the invention, and any such disclosures apply mutatis mutandis to the description of these analogues.

It should be noted that preferred modified GDF-8 molecules comprise modifications which results in a polypeptide having a sequence identity of at least 70% with GDF-8 or with a subsequence thereof of at least 10 amino acids in length. Higher sequence identities are preferred, e.g. at least 75% or even at least 80% or 85%. The sequence identity for proteins and nucleic acids can be calculated as $(N_{ref}-N_{dif})100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}$=2 and $N_{ref}$=8).

The invention also pertains to compositions useful in exercising the method of the invention. Hence, the invention also relates to an immunogenic composition comprising an immunogenically effective amount of a GDF-8 polypeptide which is a self-protein in an animal, said GDF-8 polypeptide being formulated together with an immunologically acceptable adjuvant so as to break the animal's autotolerance towards the GDF-8 polypeptide, the composition further comprising a pharmaceutically and immunologically acceptable vehicle and/or carrier. In other words, this part of the invention pertains to the formulations of naturally occurring GDF-8 polypeptides which have been described in connection with embodiments of the method of the invention.

The invention also relates to an immunogenic composition comprising an immunologically effective amount of a GDF-8 analogue defined above, said composition further comprising a pharmaceutically and immunologically acceptable diluent and/or vehicle and/or carrier and/or excipient and optionally an adjuvant. In other words, this part of the invention concerns formulations of modified GDF-8, essentially as described hereinabove. The choice of adjuvants, carriers, and vehicles is accordingly in line with what has been discussed above when referring to formulation of modified and unmodified GDF-8 for use in the inventive method for the down-regulation of GDF-8.

The polypeptides are prepared according to methods well-known in the art. Longer polypeptides are normally prepared by means of recombinant gene technology including introduction of a nucleic acid sequence encoding the GDF-8 analogue into a suitable vector, transformation of a suitable host cell with the vector, expression of the nucleic acid sequence, recovery of the expression product from the host cells or their culture supernatant, and subsequent purification and optional further modification, e.g. refolding or derivatization.

Shorter peptides are preferably prepared by means of the well-known techniques of solid- or liquid-phase peptide synthesis. However, recent advances in this technology has rendered possible the production of full-length polypeptides and proteins by these means, and therefore it is also within the scope of the present invention to prepare the long constructs by synthetic means.

Nucleic Acid Fragments and Vectors of the Invention

It will be appreciated from the above disclosure that modified GDF-8 polypeptides can be prepared by means of recombinant gene technology but also by means of chemical synthesis or semisynthesis; the latter two options are especially relevant when the modification consists in coupling to protein carriers (such as KLH, diphtheria toxoid, tetanus toxoid, and BSA) and non-proteinaceous molecules such as carbohydrate polymers and of course also when the modification comprises addition of side chains or side groups to a GDF-8 polypeptide-derived peptide chain.

For the purpose of recombinant gene technology, and of course also for the purpose of nucleic acid immunization, nucleic acid fragments encoding modified GDF-8 are important chemical products. Hence, an important part of the invention pertains to a nucleic acid fragment which encodes a GDF-8 analogue, i.e. a GDF-8 derived polypeptide which either comprises the natural GDF-8 sequence to which has been added or inserted a fusion partner or, preferably a GDF-8 derived polypeptide wherein has been introduced a foreign T-cell epitope by means of insertion and/or addition, preferably by means of substitution and/or deletion. The nucleic acid fragments of the invention are either DNA or RNA fragments.

The nucleic acid fragments of the invention will normally be inserted in suitable vectors to form cloning or expression vectors carrying the nucleic acid fragments of the invention; such novel vectors are also part of the invention. Details concerning the construction of these vectors of the invention will be discussed in context of transformed cells and microorganisms below. The vectors can, depending on purpose and type of application, be in the form of plasmids, phages, cosmids, mini-chromosomes, or virus, but also naked DNA which is only expressed transiently in certain cells is an important vector. Preferred cloning and expression vectors of the invention are capable of autonomous replication, thereby enabling high copy-numbers for the purposes of high-level expression or high-level replication for subsequent cloning.

The general outline of a vector of the invention comprises the following features in the 5'→3' direction and in operable linkage: a promoter for driving expression of the nucleic acid fragment of the invention, optionally a nucleic acid sequence encoding a leader peptide enabling secretion (to the extracellular phase or, where applicable, into the periplasma of a bacterium) of or integration into the membrane of the polypeptide fragment, the nucleic acid fragment of the invention, and optionally a nucleic acid sequence encoding a terminator. When operating with expression vectors in producer strains or cell-lines it is for the purposes of genetic stability of the transformed cell preferred that the vector when introduced into a host cell is integrated in the host cell genome. In contrast, when working with vectors to be used for effecting in vivo expression in an animal (i.e. when using the vector in DNA vaccination) it is for security reasons preferred that the vector is not incapable of being integrated in the host cell genome; typically, naked DNA or non-integrating viral vectors are used, the choices of which are well-known to the person skilled in the art.

The vectors of the invention are used to transform host cells to produce the modified GDF-8 polypeptide of the invention. Such transformed cells, which are also part of the invention, can be cultured cells or cell lines used for propagation of the nucleic acid fragments and vectors of the invention, or used for recombinant production of the modified GDF-8 polypeptides of the invention. Alternatively, the transformed cells can be suitable live vaccine strains wherein the nucleic acid fragment (one single or multiple copies) have been inserted so as to effect secretion or integration into the bacterial membrane or cell-wall of the modified GDF-8.

Preferred transformed cells of the invention are micro-organisms such as bacteria (such as the species *Escherichia* [e.g. *E. coli], Bacillus* [e.g. *Bacillus subtilis], Salmonella*, or *Mycobacterium* [preferably non-pathogenic, e.g. *M. bovis* BCG]), yeasts (such as *Saccharomyces cerevisiae*), and protozoans. Alternatively, the transformed cells are derived from a multicellular organism such as a fungus, an insect cell, a plant cell, or a mammalian cell. Recent results have shown great promise in the use of a commercially available *Drosophila melanogaster* cell line (the Schneider 2 ($S_2$) cell line and vector system available from Invitrogen) for the recombinant production of IL-5 analogues of the invention, and therefore this expression system is particularly preferred, also for the purposes of the present invention.

For the purposes of cloning and/or optimised expression it is preferred that the transformed cell is capable of replicating the nucleic acid fragment of the invention. Cells expressing the nucleic fragment are preferred useful embodiments of the invention; they can be used for small-scale or large-scale preparation of the modified GDF-8 or, in the case of nonpathogenic bacteria, as vaccine constituents in a live vaccine.

When producing the modified GDF-8 of the invention by means of transformed cells, it is convenient, although far from essential, that the expression product is either exported out into the culture medium or carried on the surface of the transformed cell.

When an effective producer cell has been identified it is preferred, on the basis thereof, to establish a stable cell line which carries the vector of the invention and which expresses the nucleic acid fragment encoding the modified GDF-8. Preferably, this stable cell line secretes or carries the GDF-8 analogue of the invention, thereby facilitating purification thereof.

In general, plasmid vectors containing replicon and control sequences which are derived from species compatible with the host cell are used in connection with the hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the prokaryotic micro-organism for expression.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EP-A-0 036 776). While these are the most commonly used, other microbial promoters have been discovered and utilized, and details concerning their nucleotide sequences have been published, enabling a skilled worker to ligate them functionally with plasmid vectors (Siebwenlist et al., 1980). Certain genes from prokaryotes may be expressed efficiently in *E. coli* from their own promoter sequences, precluding the need for addition of another promoter by artificial means.

In addition to prokaryotes, eukaryotic microbes, such as yeast cultures may also be used, and here the promoter should be capable of driving expression. *Saccharomyces cerevisiae*, or common baker's yeast is the most commonly used among eukaryotic micro-organisms, although a number of other strains are commonly available. For expression in *Saccharomyces*, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to micro-organisms, cultures of cells derived from multicellular organisms may also be used as hosts. In principle, any such cell culture is workable, whether from vertebrate or invertebrate culture. However, interest has been greatest in vertebrate cells, and propagation of vertebrate in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293, *Drosophila melanogaster* and *Spodoptera frugiperda* (SF) cells (commercially available as complete expression systems from i.a. Protein Sciences, 1000 Research Parkway, Meriden, Conn. 06450, U.S.A. and from Invitrogen), and MDCK cell lines. In the present invention, especially preferred cell lines are $S_2$ and $SF_2$, available from Invitrogen, PO Box 2312, 9704 CH Groningen, The Netherlands.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) or may be provided by the host cell chromosomal replication mechanism. If the vector is integrated into the host cell chromosome, the latter is often sufficient.

Identification of Useful GDF-8 Analogues

It will be clear to the skilled person that not all variants or modifications of native GDF-8 will have the ability to elicit antibodies in an animal which are cross-reactive with the native form. It is, however, not difficult to set up an effective standard screen for modified GDF-8 molecules which fulfil the minimum requirements for immunological reactivity discussed herein. Hence, another part of the invention concerns a method for the identification of a modified GDF-8 polypeptide which is capable of inducing antibodies against unmodified GDF-8 in an animal species where the unmodified GDF-8 polypeptide is a self-protein, the method comprising preparing, by means of peptide synthesis or by genetic engineering methods, a set of mutually distinct modified GDF-8 polypeptides wherein amino acids have been added to, inserted in, deleted from, or substituted into the amino acid sequence of a GDF-8 polypeptide of the animal species thereby giving rise to amino acid sequences in the set which comprise T-cell epitopes which are foreign to the animal species, testing members of the set for their ability to induce production of antibodies by the animal species against the unmodified GDF-8, and isolating the member(s) of the set which significantly induces antibody production against unmodified GDF-8 in the animal species.

In this context, the "set of mutually distinct modified GDF-8 polypeptides" is a collection of non-identical modified GDF-8 polypeptides which have e.g. been selected on the basis of the criteria discussed above (e.g. in combination with studies of circular dichroism, NMR spectra, and/or X-ray diffraction patterns). The set may consist of only a few members but it is contemplated that the set may contain several hundred members.

The set may be "prepared" in vivo insofar that one applicable testing system is to prepare nucleic acid fragments encoding the members and then using these nucleic acid fragments in nucleic acid immunization as described herein so as to determine whether the expression products are immunogenic. Hence, the test of members of the set can be performed in vivo, but a number of in vitro tests can be applied which narrow down the number of modified molecules which will serve the purpose of the invention.

Since the goal of introducing the foreign T-cell epitopes is to support the B-cell response by T-cell help, a prerequisite is that T-cell proliferation is induced by the modified GDF-8. T-cell proliferation can be tested by standardized proliferation assays in vitro. In short, a sample enriched for T-cells is obtained from a subject and subsequently kept in culture. The cultured T-cells are contacted with APCs of the subject which have previously taken up the modified molecule and processed it to present its T-cell epitopes. The proliferation of T-cells is monitored and compared to a suitable control (e.g. T-cells in culture contacted with APCs which have processed intact, native GDF-8). Alternatively, proliferation can be measured by determining the concentration of relevant cytokines released by the T-cells in response to their recognition of foreign T-cells.

Having rendered highly probable that at least one modified GDF-8 of the set is capable of inducing antibody production against GDF-8, it is possible to prepare an immunogenic composition comprising at least one modified GDF-8 polypeptide which is capable of inducing antibodies against unmodified GDF-8 in an animal species where the unmodified GDF-8 polypeptide is a self-protein, the method comprising admixing the member(s) of the set which significantly induces production of antibodies in the animal species which are reactive with GDF-8 with a pharmaceutically and immunologically acceptable carrier and/or vehicle and/or diluent and/or excipient, optionally in combination with at least one pharmaceutically and immunologically acceptable adjuvant.

The above aspects of the invention are conveniently carried out by initially preparing a number of mutually distinct nucleic acid sequences or vectors of the invention, inserting these into appropriate expression vectors, transforming suitable host cells with the vectors, and expressing the nucleic acid sequences of the invention. These steps can be followed by isolation of the expression products. It is preferred that the nucleic acid sequences and/or vectors are prepared by methods comprising exercise of a molecular amplification technique such as PCR or by means of nucleic acid synthesis.

Preamble to Examples

Expression of the 109 amino acid residue C-terminal region of GDF-8 fused to an N-terminal His-tag has been obtained in *E. coli* and the purified fusion protein has been used for immunisation of rabbits. Full-length GDF-8 has been expressed in CHO cells and shown to be secreted as dimers of unprocessed and processed GDF-8, respectively (McPherron et al., Nature 387, 83–90, 1997). Thus, no problems are expected with expression of the below-discussed GDF-8 autovaccine constructs. The most likely expression systems to be used for production of the GDF-8 AutoVac constructs are *E. coli*, the yeast P. pastoris and CHO cells and insect cells such as the above mentioned *Drosophila* cells.

Example 1

Vaccine Design

The rationale behind the present invention is to substitute stretches of amino acid residues in the target protein with foreign or artificial T-cell epitopes e.g. the promiscuous tetanus toxin T-cell epitopes P2 and P30. Preferably these substitutions should only minimally disturb the authentic three dimensional structure of the target protein.

The target protein here is the 109 amino acid residue C-terminal region of GDF-8, the homodimer of which is expected to be the biologically active form of GDF-8. The three-dimensional structure of this region of GDF-8 is not known but based on the structure of the homologous TGF-β protein the model of monomeric GDF-8 shown in FIG. 2 can be anticipated to be reasonably close to reality. In this model of the wild type GDF-8 (wt) α-helices are shown as cylinders and β-sheets are shown as arrows. The cysteine-residues and thus the disulfide-bonds are very closely positioned in the structure.

It should be borne in mind that the presence of the relatively high number cysteines (9) and thus disulfide-bonds in the 109 amino acid residue C-terminal region of GDF-8 limits the possible sites where the foreign T-cell epitopes can be positioned.

In addition to producing the 109 amino acid residue C-terminal region of GDF-8 without substitutions (i.e. residues 267–375 of SEQ ID NOs: 1–10), the following GDF-8 AutoVac constructs are proposed.

GDF-8 P2-1 (SEQ ID NO: 15) is the 109 amino acid residue C-terminal region of GDF-8 with amino acid residues 18–32 substituted by P2.

GDF-8 P2-2 (SEQ ID NO: 16) is the 109 amino acid residue C-terminal region of GDF-8 with amino acid residues 52–66 substituted by P2.

GDF-8 P2-3 (SEQ ID NO: 17) is the 109 amino acid residue C-terminal region of GDF-8 with amino acid residues 83–97 substituted by P2.

GDF-8 P30-1 (SEQ ID NO: 18) is the 109 amino acid residue C-terminal region of GDF-8 with amino acid residues 21–41 substituted by P30.

GDF-8 P30-2 (SEQ ID NO: 19) is the 109 amino acid residue C-terminal region of GDF-8 with amino acid residues 49–69 substituted by P30.

GDF-8 P30-3A (SEQ ID NO: 20) is the 109 amino acid residue C-terminal region of GDF-8 with amino acid residues 79–99 substituted by P30.

GDF-8 P30-3B (SEQ ID NO: 21) is the 109 amino acid residue C-terminal region of GDF-8 with amino acid residues 84–104 substituted by P30.

GDF-8 dimer (SEQ ID NO: 22) is two copies of the 109 amino acid residue C-terminal region of GDF-8 covalently connected through the P2 and P30 epitopes. In other words the molecule is comprised of two halves. The first half is the 109 amino acid residue C-terminal region of GDF-8 having P2 fused to its C-terminus while the second half is the 109 amino acid residue C-terminal region of GDF-8 having P30 fused to its N-terminus.

GDF-8 ext (SEQ ID NO: 23) consists of the C-terminal 160 amino acid residue of GDF-8 with residues 16–36 substituted by P30 and residues 37–51 substituted by P2. This construct is the 109 amino acid residue C-terminal region of GDF-8 with an N-terminal extension containing both the P2 and the P30 epitopes.

In all exemplary constructs except from the latter 2, it is contemplated to produce a variant where Cys73 is substituted with Ser to avoid dimerisation through disulfide-bond formation. In GDF-8 ext it is contemplated to perform a similar substitution in the corresponding position (i.e. Cys124→Ser124).

Example 2

In Vitro Models

It is contemplated to initially immunise mice with purified GDF-8 variants as described above. After e.g. three immunisations antibodies will be measured in ELISA using the non-modified GDF-8 molecule as the antigen. The primary reason for these initial experiments is to confirm that the AutoVac™ technology is applicable for creating anti-GDF-8 cross reactive autoantibodies and, importantly, to identify the optimal dosing and immunisation regimen. It would, however, be very surprising if antibodies against GDF-8 were not raised using the present technology, since the fundamental immunological mechanisms of such a response are most likely to be identical to those which have already been observed for TNFα, cf. WO 98/46642 and WO 95/05849.

Example 3

In Vivo Models

Groups of mice will be immunised with the various constructs described in Example 1. The mice will be immunised at the age of about 4 weeks since they have to be immune competent in order to respond to the vaccine. Freund's Complete adjuvant will be used, but experiments will also be performed using an alum adjuvant such as Adjuphos™, which has previously been used successfully in admixture with TNF autovaccine constructs. Adjuphos™ is accepted for both human and animal use. During the entire immunisation period the total body weight of GDF-8 immunised as well as control animals will be monitored regularly. When the mice are approximately 16 weeks of age, they will be sacrificed and the size of their muscle mass will be determined.

Due to the relatively narrow window in time where mice are immune competent but still not fully outgrown, it may be difficult to demonstrate an effect of anti-GDF-8 vaccination in these animals. If that proves to be the case, it is contemplated to alternatively immunise rats or larger animals such as pigs, cattle, etc.

The modified GDF-8 molecule, which superiorly increases the growth rate of the animals and/or superiorly increases the maximum muscle size, is selected for clinical development.

What is claimed is:

1. A method for in vivo down-regulation of growth differentiation factor 8 (GDF-8) activity in an animal, the method comprising administering to said animal an immunogenically effective amount of at least one GDF-8 analogue, which is a GDF-8 polypeptide that has been modified by means of at least two substitutions of a first amino acid sequence in SEQ ID NO: 11 or 12 with a second amino acid sequence which comprises a foreign $T_H$ epitope, wherein said first amino acid sequence is selected from residues 1–12, 18–41, 43–48, 49–69, or 79–104 in SEQ ID NO: 11 or 12; or at least one GDF-8 analogue, which is a GDF-8 polypeptide that has been modified by inserting at least one first amino acid sequence in SEQ ID NO: 11 or 12 with at least one second amino acid sequence which comprises a foreign $T_H$ epitope, wherein said first amino acid sequence is from one or more of residues 1–12, 18–30, 42–51, 82–86 and 105–109 in SEQ ID NO: 11 or 12.

2. The method according to claim 1, wherein the modification has as a result that a substantial fraction of GDF-8 B-cell epitopes are preserved and that at least one first moiety is introduced which effects targeting of the modified molecule to an antigen presenting cell (APC) or a B-lymphocyte, and/or at least one second moiety is introduced which stimulates the immune system and/or at least one third moiety is introduced which optimises presentation of the modified GDF-8 polypeptide to the immune system.

3. The method according to claim 2, wherein the modification includes introduction as side groups, by covalent or non-covalent binding to chemical groups in GDF-9 or a subsequence thereof, of the foreign $T_H$ epitope and/or of the first and/or of the second and/or of the third moiety.

4. The method according to claim 2 or 3, wherein the modification includes amino acid substitution or insertion thereof.

5. The method according to claim 4, wherein the modification results in the provision of a fusion polypeptide.

6. The method according to claim 4, wherein the modification results in a substantial preservation of the overall tertiary structure of GDF-8.

7. The method according to claim 2, wherein the foreign T-cell epitope is immunodominant in the animal.

8. The method according to claim 2, wherein the foreign T-cell epitope is promiscuous.

9. The method according to claim 8, wherein the foreign T-cell epitope is a natural promiscuous T-cell epitope or an artificial MHC II binding peptide sequence.

10. Previously Presented) The method according to claim 9, wherein the natural T-cell epitope is selected from a Tetanus toxoid epitope, a diphtheria toxoid epitope, an influenza virus hemagluttinin epitope, and a *P. falciparum* CS epitope.

11. The method according to claim 1, wherein the GDF-8 analogue is derived from the C-terminal, active form of GDF-8.

12. The method according to claim 1, wherein an effective amount of the GDE-8 analogue is administered to the animal via a route selected from the parenteral route such as the intradermal, the subdermal, the intracutaneous, the subcutaneous, and the intramuscular routes; the peritoneal route; the oral route; the buccal route; the sublinqual route;

the epidural route; the spinal route; the anal route; and the intracranial route.

13. The method according to claim 12, wherein the effective amount is between 0.5 μg and 2,000 μg of the GDF-8 analogue.

14. The method according to claim 12 or 13, which includes at least one administration of the GDF-8 analogue per year.

15. The method according to claims 12, wherein the GDF-8 analogue optionally has been formulated with a pharmaceutically and immunologically acceptable carrier and/or vehicle and has been formulated with an adjuvant which facilitates breaking of autotolerance to autoantigens, such as an adjuvant selected from the group consisting of an immune targeting adjuvant; an immune modulating adjuvant, a cytokine and a mycobacterial derivative; an oil formulation; a polymer; a micelle forming adjuvant; a saponin; an immunostimulating complex matrix (an ISCOM matrix); a particle; DDA; aluminium adjuvants; DNA adjuvants; γ-inulin; and an encapsulating adjuvant.

16. The method according to claim 13, wherein the GDE-8 analogue is contained in a virtual lymph node (VLN) device.

17. A method for increasing the muscle mass of an animal, the method comprising down-regulating GDF-8 activity according to the method of claim 1 to such an extent such that the muscle mass is increased at least 5% when compared to animals which exhibit normal GDF-8 activity.

18. The method according to claim 1, wherein the GDF-8 analogue is introduced without a carrier molecule.

19. The method according to claim 1, wherein the GDF-8 analogue or the modified GDF-S polypeptide optionally has been formulated with a pharmacutically and immunologically acceptable carrier and/or vehicle and has been formulated with an adjuvant which facilitates breaking of autotolerance to autoantigens wherein said adjuvant is an aluminium adjuvant.

20. The method according to claim 9, wherein the natural T-cell epitope is a tetanus toxoid epitope.

21. The method according to claim 1, wherein the GDF-8 analogue is derived from the C-terminal, active form of bovine GDF-8 polypeptide.

22. The method according to claim 20, wherein the tetanus toxoid epitope is selected from P2 (SEQ ID NO: 13) and P30 (SEQ B NO: 14).

23. A method according to claim 1, wherein the animal is a human being.

24. The method according to claim 14, wherein the GDF-8 analogue is administered at least 2, at least 3, at least 4, at least 6, or at least 12 times a year.

25. The method according to claim 11, wherein the GDF-8 analogue is derived from bovine, porcine, human, chicken, sheep or turkey GDF-8 polypeptide.

26. The method according to claim 15, wherein the immune modulating adjuvant is a toxin.

27. The method according to claim 17, wherein the GDF-8 activity is down-regulated to such an extent that muscle mass is increased 10, 15, 20, 25, 30, 35, 40 or 45% when compared to animals that exhibit normal GDF-8 activity.

28. The method according to any one of claims 1, 2, 3, 5, 6, 7, 10, 11 12, 13, 15, 16, 17, or 18–27, wherein the substitution is made in more than one of the residues 1–12, 18–41, 43–48, 49–69 or 79–104 in SEQ ID NO. 12.

* * * * *

SEQUENCE LISTING

<160> NUMBER OF SEQ ID NOS: 24

<210> SEQ ID NO 1
<211> LENGTH: 375
<212> TYPE: PRT
<213> ORGANISM: Homo sapiens

<400> SEQUENCE: 1

Met Gln Lys Leu Gln Leu Cys Val Tyr Ile Tyr Leu Phe Met Leu Ile
1 5 10 15

Val Ala Gly Pro Val Asp Leu Asn Glu Asn Ser Glu Gln Lys Glu Asn
20 25 30

Val Glu Lys Glu Gly Leu Cys Asn Ala Cys Thr Trp Arg Gln Asn Thr
35 40 45

Lys Ser Ser Arg Ile Glu Ala Ile Lys Ile Gln Ile Leu Ser Lys Leu
50 55 60

Arg Leu Glu Thr Ala Pro Asn Ile Ser Lys Asp Val Ile Arg Gln Leu
65 70 75 80

Leu Pro Lys Ala Pro Pro Leu Arg Glu Leu Ile Asp Gln Tyr Asp Val
85 90 95

Gln Arg Asp Asp Ser Ser Asp Gly Ser Leu Glu Asp Asp Asp Tyr His
100 105 110

Ala Thr Thr Glu Thr Ile Ile Thr Met Pro Thr Glu Ser Asp Phe Leu
115 120 125

Met Gln Val Asp Gly Lys Pro Lys Cys Cys Phe Phe Lys Phe Ser Ser
130 135 140

Lys Ile Gln Tyr Asn Lys Val Val Lys Ala Gln Leu Trp Ile Tyr Leu
145 150 155 160

Arg Pro Val Glu Thr Pro Thr Thr Val Phe Val Gln Ile Leu Arg Leu
165 170 175

Ile Lys Pro Met Lys Asp Gly Thr Arg Tyr Thr Gly Ile Arg Ser Leu
180 185 190

Lys Leu Asp Met Asn Pro Gly Thr Gly Ile Trp Gln Ser Ile Asp Val
195 200 205

Lys Thr Val Leu Gln Asn Trp Leu Lys Gln Pro Glu Ser Asn Leu Gly
210 215 220

Ile Glu Ile Lys Ala Leu Asp Glu Asn Gly His Asp Leu Ala Val Thr
225 230 235 240

Phe Pro Gly Pro Gly Glu Asp Gly Leu Asn Pro Phe Leu Glu Val Lys
245 250 255

Val Thr Asp Thr Pro Lys Arg Ser Arg Arg Asp Phe Gly Leu Asp Cys
260 265 270

Asp Glu His Ser Thr Glu Ser Arg Cys Cys Arg Tyr Pro Leu Thr Val
275 280 285

Asp Phe Glu Ala Phe Gly Trp Asp Trp Ile Ile Ala Pro Lys Arg Tyr
290 295 300

Lys Ala Asn Tyr Cys Ser Gly Glu Cys Glu Phe Val Phe Leu Gln Lys
305 310 315 320

Tyr Pro His Thr His Leu Val His Gln Ala Asn Pro Arg Gly Ser Ala
325 330 335

Gly Pro Cys Cys Thr Pro Thr Lys Met Ser Pro Ile Asn Met Leu Tyr
340 345 350

-continued

Phe Asn Gly Lys Glu Gln Ile Ile Tyr Gly Lys Ile Pro Ala Met Val
355 360 365

Val Asp Arg Cys Gly Cys Ser
370 375

<210> SEQ ID NO 2
<211> LENGTH: 362
<212> TYPE: PRT
<213> ORGANISM: Meleagris gallopavo

<400> SEQUENCE: 2

Met Gln Ile Leu Val His Pro Val Ala Leu Asp Gly Ser Ser Gln Pro
1 5 10 15

Thr Glu Asn Ala Glu Lys Asp Gly Leu Cys Asn Ala Cys Thr Trp Arg
20 25 30

Gln Asn Thr Lys Ser Ser Arg Ile Glu Ala Ile Lys Ile Gln Ile Leu
35 40 45

Ser Lys Leu Arg Leu Glu Gln Ala Pro Asn Ile Ser Arg Asp Val Ile
50 55 60

Lys Gln Leu Leu Pro Lys Ala Pro Pro Leu Gln Glu Leu Ile Asp Gln
65 70 75 80

Tyr Asp Val Gln Arg Asp Asp Ser Ser Asp Gly Ser Leu Glu Asp Asp
85 90 95

Asp Tyr His Ala Thr Thr Glu Thr Ile Ile Thr Met Pro Thr Glu Ser
100 105 110

Asp Phe Leu Val Gln Met Glu Gly Lys Pro Lys Cys Cys Phe Phe Lys
115 120 125

Phe Ser Ser Lys Ile Gln Tyr Asn Lys Val Val Lys Ala Gln Leu Trp
130 135 140

Ile Tyr Leu Arg Gln Val Gln Lys Pro Thr Thr Val Phe Val Gln Ile
145 150 155 160

Leu Arg Leu Ile Lys Pro Met Lys Asp Gly Thr Arg Tyr Thr Gly Ile
165 170 175

Arg Ser Leu Lys Leu Asp Met Asn Pro Gly Thr Gly Ile Trp Gln Ser
180 185 190

Ile Asp Val Lys Thr Val Leu Gln Asn Trp Leu Lys Gln Pro Glu Ser
195 200 205

Asn Leu Gly Ile Glu Ile Lys Ala Phe Asp Glu Asn Gly Arg Asp Leu
210 215 220

Ala Val Thr Phe Pro Gly Pro Gly Glu Asp Gly Leu Asn Pro Phe Leu
225 230 235 240

Glu Val Arg Val Thr Asp Thr Pro Lys Arg Ser Arg Arg Asp Phe Gly
245 250 255

Leu Asp Cys Asp Glu His Ser Thr Glu Ser Arg Cys Cys Arg Tyr Pro
260 265 270

Leu Thr Val Asp Phe Glu Ala Phe Gly Trp Asp Trp Ile Ile Ala Pro
275 280 285

Lys Arg Tyr Lys Ala Asn Tyr Cys Ser Gly Glu Cys Glu Phe Val Phe
290 295 300

Leu Gln Lys Tyr Pro His Thr His Leu Val His Gln Ala Asn Pro Arg
305 310 315 320

Gly Ser Ala Gly Pro Cys Cys Thr Pro Thr Lys Met Ser Pro Ile Asn
325 330 335

-continued

```
Met Leu Tyr Phe Asn Gly Lys Glu Gln Ile Ile Tyr Gly Lys Ile Pro
            340                 345                 350

Ala Met Val Val Asp Arg Cys Gly Cys Ser
        355                 360


<210> SEQ ID NO 3
<211> LENGTH: 375
<212> TYPE: PRT
<213> ORGANISM: Gallus sp.

<400> SEQUENCE: 3

Met Gln Lys Leu Ala Val Tyr Val Tyr Ile Tyr Leu Phe Met Gln Ile
  1               5                  10                  15

Ala Val Asp Pro Val Ala Leu Asp Gly Ser Ser Gln Pro Thr Glu Asn
            20                  25                  30

Ala Glu Lys Asp Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Gln Ala Pro Asn Ile Ser Arg Asp Val Ile Lys Gln Leu
 65                  70                  75                  80

Leu Pro Lys Ala Pro Pro Leu Gln Glu Leu Ile Asp Gln Tyr Asp Val
                85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Val Gln Met Glu Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Gln Val Gln Lys Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Phe Asp Glu Thr Gly Arg Asp Leu Ala Val Thr
225                 230                 235                 240

Phe Pro Gly Pro Gly Glu Asp Gly Leu Asn Pro Phe Leu Glu Val Arg
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335
```

-continued

Gly Pro Cys Cys Thr Pro Thr Lys Met Ser Pro Ile Asn Met Leu Tyr
340 345 350

Phe Asn Gly Lys Glu Gln Ile Ile Tyr Gly Lys Ile Pro Ala Met Val
355 360 365

Val Asp Arg Cys Gly Cys Ser
370 375

<210> SEQ ID NO 4
<211> LENGTH: 376
<212> TYPE: PRT
<213> ORGANISM: Mus musculus

<400> SEQUENCE: 4

Met Met Gln Lys Leu Gln Met Tyr Val Tyr Ile Tyr Leu Phe Met Leu
1 5 10 15

Ile Ala Ala Gly Pro Val Asp Leu Asn Glu Gly Ser Glu Arg Glu Glu
20 25 30

Asn Val Glu Lys Glu Gly Leu Cys Asn Ala Cys Ala Trp Arg Gln Asn
35 40 45

Thr Arg Tyr Ser Arg Ile Glu Ala Ile Lys Ile Gln Ile Leu Ser Lys
50 55 60

Leu Arg Leu Glu Thr Ala Pro Asn Ile Ser Lys Asp Ala Ile Arg Gln
65 70 75 80

Leu Leu Pro Arg Ala Pro Pro Leu Arg Glu Leu Ile Asp Gln Tyr Asp
85 90 95

Val Gln Arg Asp Asp Ser Ser Asp Gly Ser Leu Glu Asp Asp Asp Tyr
100 105 110

His Ala Thr Thr Glu Thr Ile Ile Thr Met Pro Thr Glu Ser Asp Phe
115 120 125

Leu Met Gln Ala Asp Gly Lys Pro Lys Cys Cys Phe Phe Lys Phe Ser
130 135 140

Ser Lys Ile Gln Tyr Asn Lys Val Val Lys Ala Gln Leu Trp Ile Tyr
145 150 155 160

Leu Arg Pro Val Lys Thr Pro Thr Thr Val Phe Val Gln Ile Leu Arg
165 170 175

Leu Ile Lys Pro Met Lys Asp Gly Thr Arg Tyr Thr Gly Ile Arg Ser
180 185 190

Leu Lys Leu Asp Met Ser Pro Gly Thr Gly Ile Trp Gln Ser Ile Asp
195 200 205

Val Lys Thr Val Leu Gln Asn Trp Leu Lys Gln Pro Glu Ser Asn Leu
210 215 220

Gly Ile Glu Ile Lys Ala Leu Asp Glu Asn Gly His Asp Leu Ala Val
225 230 235 240

Thr Phe Pro Gly Pro Gly Glu Asp Gly Leu Asn Pro Phe Leu Glu Val
245 250 255

Lys Val Thr Asp Thr Pro Lys Arg Ser Arg Arg Asp Phe Gly Leu Asp
260 265 270

Cys Asp Glu His Ser Thr Glu Ser Arg Cys Cys Arg Tyr Pro Leu Thr
275 280 285

Val Asp Phe Glu Ala Phe Gly Trp Asp Trp Ile Ile Ala Pro Lys Arg
290 295 300

Tyr Lys Ala Asn Tyr Cys Ser Gly Glu Cys Glu Phe Val Phe Leu Gln
305 310 315 320

-continued

```
Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
            340                 345                 350

Tyr Phe Asn Gly Lys Glu Gln Ile Ile Tyr Gly Lys Ile Pro Ala Met
        355                 360                 365

Val Val Asp Arg Cys Gly Cys Ser
    370                 375


<210> SEQ ID NO 5
<211> LENGTH: 375
<212> TYPE: PRT
<213> ORGANISM: Bos taurus

<400> SEQUENCE: 5

Met Gln Lys Leu Gln Ile Ser Val Tyr Ile Tyr Leu Phe Met Leu Ile
  1               5                  10                  15

Val Ala Gly Pro Val Asp Leu Asn Glu Asn Ser Glu Gln Lys Glu Asn
             20                  25                  30

Val Glu Lys Glu Gly Leu Cys Asn Ala Cys Leu Trp Arg Glu Asn Thr
         35                  40                  45

Thr Ser Ser Arg Leu Glu Ala Ile Lys Ile Gln Ile Leu Ser Lys Leu
     50                  55                  60

Arg Leu Glu Thr Ala Pro Asn Ile Ser Lys Asp Ala Ile Arg Gln Leu
 65                  70                  75                  80

Leu Pro Lys Ala Pro Pro Leu Leu Glu Leu Ile Asp Gln Phe Asp Val
                 85                  90                  95

Gln Arg Asp Ala Ser Ser Asp Gly Ser Leu Glu Asp Asp Asp Tyr His
            100                 105                 110

Ala Arg Thr Glu Thr Val Ile Thr Met Pro Thr Glu Ser Asp Leu Leu
        115                 120                 125

Thr Gln Val Glu Gly Lys Pro Lys Cys Cys Phe Phe Lys Phe Ser Ser
    130                 135                 140

Lys Ile Gln Tyr Asn Lys Leu Val Lys Ala Gln Leu Trp Ile Tyr Leu
145                 150                 155                 160

Arg Pro Val Lys Thr Pro Ala Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Glu Pro Gly Glu Asp Gly Leu Thr Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300
```

-continued

```
Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Glu Gly Gln Ile Ile Tyr Gly Lys Ile Pro Ala Met Val
        355                 360                 365

Val Asp Arg Cys Gly Cys Ser
    370                 375


<210> SEQ ID NO 6
<211> LENGTH: 375
<212> TYPE: PRT
<213> ORGANISM: Ovis sp.

<400> SEQUENCE: 6

Met Gln Lys Leu Gln Ile Phe Val Tyr Ile Tyr Leu Phe Met Leu Leu
  1               5                  10                  15

Val Ala Gly Pro Val Asp Leu Asn Glu Asn Ser Glu Gln Lys Glu Asn
             20                  25                  30

Val Glu Lys Lys Gly Leu Cys Asn Ala Cys Leu Trp Arg Gln Asn Asn
         35                  40                  45

Lys Ser Ser Arg Leu Glu Ala Ile Lys Ile Gln Ile Leu Ser Lys Leu
     50                  55                  60

Arg Leu Glu Thr Ala Pro Asn Ile Ser Lys Asp Ala Ile Arg Gln Leu
 65                  70                  75                  80

Leu Pro Lys Ala Pro Pro Leu Arg Glu Leu Ile Asp Gln Tyr Asp Val
                 85                  90                  95

Gln Arg Asp Asp Ser Ser Asp Gly Ser Leu Glu Asp Asp Asp Tyr His
            100                 105                 110

Val Thr Thr Glu Thr Val Ile Thr Met Pro Thr Glu Ser Asp Leu Leu
        115                 120                 125

Ala Glu Val Gln Glu Lys Pro Lys Cys Cys Phe Phe Lys Phe Ser Ser
    130                 135                 140

Lys Ile Gln His Asn Lys Val Val Lys Ala Gln Leu Trp Ile Tyr Leu
145                 150                 155                 160

Arg Pro Val Lys Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Glu Pro Gly Glu Glu Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285
```

-continued

```
Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Leu Phe Leu Gln Lys
305                 310                 315                 320

Tyr Pro His Thr His Leu Val His Gln Ala Asn Pro Lys Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Gly Met Val
        355                 360                 365

Val Asp Arg Cys Gly Cys Ser
    370                 375


<210> SEQ ID NO 7
<211> LENGTH: 376
<212> TYPE: PRT
<213> ORGANISM: Rattus norvegicus

<400> SEQUENCE: 7

Met Ile Gln Lys Pro Gln Met Tyr Val Tyr Ile Tyr Leu Phe Val Leu
  1               5                  10                  15

Ile Ala Ala Gly Pro Val Asp Leu Asn Glu Asp Ser Glu Arg Glu Ala
                 20                  25                  30

Asn Val Glu Lys Glu Gly Leu Cys Asn Ala Cys Ala Trp Arg Gln Asn
         35                  40                  45

Thr Arg Tyr Ser Arg Ile Glu Ala Ile Lys Ile Gln Ile Leu Ser Lys
     50                  55                  60

Leu Arg Leu Glu Thr Ala Pro Asn Ile Ser Lys Asp Ala Ile Arg Gln
 65                  70                  75                  80

Leu Leu Pro Arg Ala Pro Pro Leu Arg Glu Leu Ile Asp Gln Tyr Asp
                 85                  90                  95

Val Gln Arg Asp Asp Ser Ser Asp Gly Ser Leu Glu Asp Asp Asp Tyr
            100                 105                 110

His Ala Thr Thr Glu Thr Ile Ile Thr Met Pro Thr Glu Ser Asp Phe
        115                 120                 125

Leu Met Gln Ala Asp Gly Lys Pro Lys Cys Cys Phe Phe Lys Phe Ser
    130                 135                 140

Ser Lys Ile Gln Tyr Asn Lys Val Val Lys Ala Gln Leu Trp Ile Tyr
145                 150                 155                 160

Leu Arg Ala Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
        195                 200                 205

Val Lys Thr Val Leu Gln Asn Trp Leu Lys Gln Pro Glu Ser Asn Leu
    210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg Asp Phe Gly Leu Asp
            260                 265                 270
```

-continued

```
Cys Asp Glu His Ser Thr Glu Ser Arg Cys Cys Arg Tyr Pro Leu Thr
        275                 280                 285

Val Asp Phe Glu Ala Phe Gly Trp Asp Trp Ile Ile Ala Pro Lys Arg
    290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
            340                 345                 350

Tyr Phe Asn Gly Lys Glu Gln Ile Ile Tyr Gly Lys Ile Pro Ala Met
        355                 360                 365

Val Val Asp Arg Cys Gly Cys Ser
    370                 375


<210> SEQ ID NO 8
<211> LENGTH: 375
<212> TYPE: PRT
<213> ORGANISM: Sus scrofa

<400> SEQUENCE: 8

Met Gln Lys Leu Gln Ile Tyr Val Tyr Ile Tyr Leu Phe Met Leu Ile
  1               5                  10                  15

Val Ala Gly Pro Val Asp Leu Asn Glu Asn Ser Glu Gln Lys Glu Asn
             20                  25                  30

Val Glu Lys Glu Gly Leu Cys Asn Ala Cys Met Trp Arg Gln Asn Thr
         35                  40                  45

Lys Ser Ser Arg Leu Glu Ala Ile Lys Ile Gln Ile Leu Ser Lys Leu
     50                  55                  60

Arg Leu Glu Thr Ala Pro Asn Ile Ser Lys Asp Ala Ile Arg Gln Leu
 65                  70                  75                  80

Leu Pro Lys Ala Pro Pro Leu Arg Glu Leu Ile Asp Gln Tyr Asp Val
                 85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Leu Leu
        115                 120                 125

Met Gln Val Glu Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Lys Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255
```

-continued

```
Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
    370                 375


<210> SEQ ID NO 9
<211> LENGTH: 374
<212> TYPE: PRT
<213> ORGANISM: Danio rerio

<400> SEQUENCE: 9

Met His Phe Thr Gln Val Leu Ile Ser Leu Ser Val Leu Ile Ala Cys
  1               5                  10                  15

Gly Pro Val Gly Tyr Gly Asp Ile Thr Ala His Gln Gln Pro Ser Thr
            20                  25                  30

Ala Thr Glu Glu Ser Glu Leu Cys Ser Thr Cys Glu Phe Arg Gln His
        35                  40                  45

Ser Lys Leu Met Arg Leu His Ala Ile Lys Ser Gln Ile Leu Ser Lys
     50                  55                  60

Leu Arg Leu Lys Gln Ala Pro Asn Ile Ser Arg Asp Val Val Lys Gln
 65                  70                  75                  80

Leu Leu Pro Lys Ala Pro Pro Leu Gln Gln Leu Leu Asp Gln Tyr Asp
                 85                  90                  95

Val Leu Gly Asp Asp Ser Lys Asp Gly Ala Val Glu Glu Asp Asp Glu
            100                 105                 110

His Ala Thr Thr Glu Thr Ile Met Thr Met Ala Thr Glu Pro Asp Pro
        115                 120                 125

Ile Val Gln Val Asp Arg Lys Pro Lys Cys Cys Phe Phe Ser Phe Ser
    130                 135                 140

Pro Lys Ile Gln Ala Asn Arg Ile Val Arg Ala Gln Leu Trp Val His
145                 150                 155                 160

Leu Arg Pro Ala Glu Glu Ala Thr Thr Val Phe Leu Gln Ile Ser Arg
                165                 170                 175

Leu Met Pro Val Lys Asp Gly Gly Arg His Arg Ile Arg Ser Leu Lys
            180                 185                 190

Ile Asp Val Asn Ala Gly Val Thr Ser Trp Gln Ser Ile Asp Val Lys
        195                 200                 205

Gln Val Leu Thr Val Trp Leu Lys Gln Pro Glu Thr Asn Arg Gly Ile
    210                 215                 220

Glu Ile Asn Ala Tyr Asp Ala Lys Gly Asn Asp Leu Ala Val Thr Ser
225                 230                 235                 240
```

-continued

```
Thr Glu Thr Gly Glu Asp Gly Leu Leu Pro Phe Met Glu Val Lys Ile
                245                 250                 255

Ser Glu Gly Pro Lys Arg Ile Arg Arg Asp Ser Gly Leu Asp Cys Asp
            260                 265                 270

Glu Asn Ser Ser Glu Ser Arg Cys Cys Arg Tyr Pro Leu Thr Val Asp
        275                 280                 285

Phe Glu Asp Phe Gly Trp Asp Trp Ile Ile Ala Pro Lys Arg Tyr Lys
    290                 295                 300

Ala Asn Tyr Cys Ser Gly Glu Cys Asp Tyr Met Tyr Leu Gln Lys Tyr
305                 310                 315                 320

Pro His Thr His Leu Val Asn Lys Ala Ser Pro Arg Gly Thr Ala Gly
                325                 330                 335

Pro Cys Cys Thr Pro Thr Lys Met Ser Pro Ile Asn Met Leu Tyr Phe
            340                 345                 350

Asn Gly Lys Glu Gln Ile Ile Tyr Gly Lys Ile Pro Ser Met Val Val
        355                 360                 365

Asp Arg Cys Gly Cys Ser
    370


<210> SEQ ID NO 10
<211> LENGTH: 375
<212> TYPE: PRT
<213> ORGANISM: Papio hamadryas

<400> SEQUENCE: 10

Met Gln Lys Leu Gln Leu Cys Val Tyr Ile Tyr Leu Phe Met Leu Ile
  1               5                  10                  15

Val Ala Gly Pro Val Asp Leu Asn Glu Asn Ser Glu Gln Lys Glu Asn
             20                  25                  30

Val Glu Lys Glu Gly Leu Cys Asn Ala Cys Thr Trp Arg Gln Asn Thr
         35                  40                  45

Lys Ser Ser Arg Ile Glu Ala Ile Lys Ile Gln Ile Leu Ser Lys Leu
     50                  55                  60

Arg Leu Glu Thr Ala Pro Asn Ile Ser Lys Asp Ala Ile Arg Gln Leu
 65                  70                  75                  80

Leu Pro Lys Ala Pro Pro Leu Arg Glu Leu Ile Asp Gln Tyr Asp Val
                 85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220
```

-continued

```
Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Leu Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
    370                 375


<210> SEQ ID NO 11
<211> LENGTH: 109
<212> TYPE: PRT
<213> ORGANISM: Homo sapiens
<220> FEATURE:
<221> NAME/KEY: PEPTIDE
<222> LOCATION: (1)..(109)
<223> OTHER INFORMATION: Identical to residues 267-375 in SEQ ID NO: 1

<400> SEQUENCE: 11

Asp Phe Gly Leu Asp Cys Asp Glu His Ser Thr Glu Ser Arg Cys Cys
  1               5                  10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
     50                  55                  60

Asn Pro Arg Gly Ser Ala Gly Pro Cys Cys Thr Pro Thr Lys Met Ser
 65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105


<210> SEQ ID NO 12
<211> LENGTH: 109
<212> TYPE: PRT
<213> ORGANISM: Bos taurus
<220> FEATURE:
<221> NAME/KEY: PEPTIDE
<222> LOCATION: (1)..(109)
<223> OTHER INFORMATION: Identical to residues 267-375 in SEQ ID NO: 5

<400> SEQUENCE: 12

Asp Phe Gly Leu Asp Cys Asp Glu His Ser Thr Glu Ser Arg Cys Cys
  1               5                  10                  15
```

-continued

Arg Tyr Pro Leu Thr Val Asp Phe Glu Ala Phe Gly Trp Asp Trp Ile
20 25 30

Ile Ala Pro Lys Arg Tyr Lys Ala Asn Tyr Cys Ser Gly Glu Cys Glu
35 40 45

Phe Val Phe Leu Gln Lys Tyr Pro His Thr His Leu Val His Gln Ala
50 55 60

Asn Pro Arg Gly Ser Ala Gly Pro Cys Cys Thr Pro Thr Lys Met Ser
65 70 75 80

Pro Ile Asn Met Leu Tyr Phe Asn Gly Glu Gly Gln Ile Ile Tyr Gly
85 90 95

Lys Ile Pro Ala Met Val Val Asp Arg Cys Gly Cys Ser
100 105

<210> SEQ ID NO 13
<211> LENGTH: 15
<212> TYPE: PRT
<213> ORGANISM: Clostridium tetani

<400> SEQUENCE: 13

Gln Tyr Ile Lys Ala Asn Ser Lys Phe Ile Gly Ile Thr Glu Leu
1 5 10 15

<210> SEQ ID NO 14
<211> LENGTH: 21
<212> TYPE: PRT
<213> ORGANISM: Clostridium tetani

<400> SEQUENCE: 14

Phe Asn Asn Phe Thr Val Ser Phe Trp Leu Arg Val Pro Lys Val Ser
1 5 10 15

Ala Ser His Leu Glu
20

<210> SEQ ID NO 15
<211> LENGTH: 109
<212> TYPE: PRT
<213> ORGANISM: Artificial sequence
<220> FEATURE:
<221> NAME/KEY: MUTAGEN
<222> LOCATION: (18)..(32)
<223> OTHER INFORMATION: Tetanus toxoid P2 epitope (SEQ ID NO: 13)
<220> FEATURE:
<221> NAME/KEY: SIMILAR
<222> LOCATION: (1)..(17)
<223> OTHER INFORMATION: Identical to residues 267-283 in SEQ ID NO: 1
<220> FEATURE:
<221> NAME/KEY: SIMILAR
<222> LOCATION: (33)..(109)
<223> OTHER INFORMATION: Identical to residues 299-375 in SEQ ID NO: 1
<220> FEATURE:
<221> NAME/KEY: SITE
<222> LOCATION: (73)
<223> OTHER INFORMATION: Cys or Ser
<220> FEATURE:
<221> NAME/KEY: SITE
<222> LOCATION: (90)..(91)
<223> OTHER INFORMATION: Lys Glu or Glu Gly

<400> SEQUENCE: 15

Asp Phe Gly Leu Asp Cys Asp Glu His Ser Thr Glu Ser Arg Cys Cys
1 5 10 15

Arg Gln Tyr Ile Lys Ala Asn Ser Lys Phe Ile Gly Ile Thr Glu Leu
20 25 30

Ile Ala Pro Lys Arg Tyr Lys Ala Asn Tyr Cys Ser Gly Glu Cys Glu
35 40 45

-continued

```
Phe Val Phe Leu Gln Lys Tyr Pro His Thr His Leu Val His Gln Ala
     50                  55                  60

Asn Pro Arg Gly Ser Ala Gly Pro Cys Cys Thr Pro Thr Lys Met Ser
 65                  70                  75                  80

Pro Ile Asn Met Leu Tyr Phe Asn Gly Lys Glu Gln Ile Ile Tyr Gly
                 85                  90                  95

Lys Ile Pro Ala Met Val Val Asp Arg Cys Gly Cys Ser
            100                 105


<210> SEQ ID NO 16
<211> LENGTH: 109
<212> TYPE: PRT
<213> ORGANISM: Artificial sequence
<220> FEATURE:
<221> NAME/KEY: MUTAGEN
<222> LOCATION: (52)..(66)
<223> OTHER INFORMATION: Tetanus toxoid P2 epitope (SEQ ID NO: 13)
<220> FEATURE:
<221> NAME/KEY: SIMILAR
<222> LOCATION: (1)..(51)
<223> OTHER INFORMATION: Identical to residues 267-317 in SEQ ID NO: 1
<220> FEATURE:
<221> NAME/KEY: SIMILAR
<222> LOCATION: (67)..(109)
<223> OTHER INFORMATION: Identical to residues 333-375 in SEQ ID NO: 1
<220> FEATURE:
<221> NAME/KEY: SITE
<222> LOCATION: (73)
<223> OTHER INFORMATION: Cys or Ser
<220> FEATURE:
<221> NAME/KEY: SITE
<222> LOCATION: (90)..(91)
<223> OTHER INFORMATION: Lys Glu or Glu Gly

<400> SEQUENCE: 16

Asp Phe Gly Leu Asp Cys Asp Glu His Ser Thr Glu Ser Arg Cys Cys
  1               5                  10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Gln Tyr Ile Lys Ala Asn Ser Lys Phe Ile Gly Ile Thr
     50                  55                  60

Glu Leu Arg Gly Ser Ala Gly Pro Cys Cys Thr Pro Thr Lys Met Ser
 65                  70                  75                  80

Pro Ile Asn Met Leu Tyr Phe Asn Gly Lys Glu Gln Ile Ile Tyr Gly
                 85                  90                  95

Lys Ile Pro Ala Met Val Val Asp Arg Cys Gly Cys Ser
            100                 105


<210> SEQ ID NO 17
<211> LENGTH: 109
<212> TYPE: PRT
<213> ORGANISM: Artificial sequence
<220> FEATURE:
<221> NAME/KEY: MUTAGEN
<222> LOCATION: (83)..(97)
<223> OTHER INFORMATION: Tetanus toxoid P2 epitope (SEQ ID NO: 13)
<220> FEATURE:
<221> NAME/KEY: SIMILAR
<222> LOCATION: (1)..(82)
<223> OTHER INFORMATION: Identical to residues 267-348 in SEQ ID NO: 1
<220> FEATURE:
<221> NAME/KEY: SIMILAR
<222> LOCATION: (98)..(109)
<223> OTHER INFORMATION: Identical to residues 364-375 in SEQ ID NO: 1
```

-continued

<220> FEATURE:
<221> NAME/KEY: SITE
<222> LOCATION: (73)
<223> OTHER INFORMATION: Cys or Ser
<220> FEATURE:
<221> NAME/KEY: SITE
<222> LOCATION: (90)..(91)
<223> OTHER INFORMATION: Lys Glu or Glu Gly

<400> SEQUENCE: 17

```
Asp Phe Gly Leu Asp Cys Asp Glu His Ser Thr Glu Ser Arg Cys Cys
  1               5                  10                  15

Arg Tyr Pro Leu Thr Val Asp Phe Glu Ala Phe Gly Trp Asp Trp Ile
             20                  25                  30

Ile Ala Pro Lys Arg Tyr Lys Ala Asn Tyr Cys Ser Gly Glu Cys Glu
         35                  40                  45

Phe Val Phe Leu Gln Lys Tyr Pro His Thr His Leu Val His Gln Ala
     50                  55                  60

Asn Pro Arg Gly Ser Ala Gly Pro Cys Cys Thr Pro Thr Lys Met Ser
 65                  70                  75                  80

Pro Ile Gln Tyr Ile Lys Ala Asn Ser Lys Phe Ile Gly Ile Thr Glu
                 85                  90                  95

Leu Ile Pro Ala Met Val Val Asp Arg Cys Gly Cys Ser
            100                 105
```

<210> SEQ ID NO 18
<211> LENGTH: 109
<212> TYPE: PRT
<213> ORGANISM: Artificial sequence
<220> FEATURE:
<221> NAME/KEY: MUTAGEN
<222> LOCATION: (21)..(41)
<223> OTHER INFORMATION: Tetanus toxoid P30 epitope (SEQ ID NO: 14)
<220> FEATURE:
<221> NAME/KEY: SIMILAR
<222> LOCATION: (42)..(109)
<223> OTHER INFORMATION: Identical to residues 307-375 in SEQ ID NO: 1
<220> FEATURE:
<221> NAME/KEY: SIMILAR
<222> LOCATION: (42)..(109)
<223> OTHER INFORMATION: Identical to residues 308-375 in SEQ ID NO: 1
<220> FEATURE:
<221> NAME/KEY: SITE
<222> LOCATION: (73)
<223> OTHER INFORMATION: Cys or Ser
<220> FEATURE:
<221> NAME/KEY: SITE
<222> LOCATION: (90)..(91)
<223> OTHER INFORMATION: Lys Glu or Glu Gly

<400> SEQUENCE: 18

```
Asp Phe Gly Leu Asp Cys Asp Glu His Ser Thr Glu Ser Arg Cys Cys
  1               5                  10                  15

Arg Tyr Pro Leu Phe Asn Asn Phe Thr Val Ser Phe Trp Leu Arg Val
             20                  25                  30

Pro Lys Val Ser Ala Ser His Leu Glu Tyr Cys Ser Gly Glu Cys Glu
         35                  40                  45

Phe Val Phe Leu Gln Lys Tyr Pro His Thr His Leu Val His Gln Ala
     50                  55                  60

Asn Pro Arg Gly Ser Ala Gly Pro Cys Cys Thr Pro Thr Lys Met Ser
 65                  70                  75                  80

Pro Ile Asn Met Leu Tyr Phe Asn Gly Lys Glu Gln Ile Ile Tyr Gly
                 85                  90                  95
```

-continued

```
Lys Ile Pro Ala Met Val Val Asp Arg Cys Gly Cys Ser
            100                 105


<210> SEQ ID NO 19
<211> LENGTH: 109
<212> TYPE: PRT
<213> ORGANISM: Artificial sequence
<220> FEATURE:
<221> NAME/KEY: MUTAGEN
<222> LOCATION: (49)..(69)
<223> OTHER INFORMATION: Tetanus toxoid P30 epitope (SEQ ID NO: 14)
<220> FEATURE:
<221> NAME/KEY: SIMILAR
<222> LOCATION: (1)..(48)
<223> OTHER INFORMATION: Identical to residues 267-314 in SEQ ID NO: 1
<220> FEATURE:
<221> NAME/KEY: SIMILAR
<222> LOCATION: (70)..(109)
<223> OTHER INFORMATION: Identical to residues 336-375 in SEQ ID NO: 1
<220> FEATURE:
<221> NAME/KEY: SITE
<222> LOCATION: (73)
<223> OTHER INFORMATION: Cys or Ser
<220> FEATURE:
<221> NAME/KEY: SITE
<222> LOCATION: (90)..(91)
<223> OTHER INFORMATION: Lys Glu or Glu Gly

<400> SEQUENCE: 19

Asp Phe Gly Leu Asp Cys Asp Glu His Ser Thr Glu Ser Arg Cys Cys
  1               5                  10                  15

Arg Tyr Pro Leu Thr Val Asp Phe Glu Ala Phe Gly Trp Asp Trp Ile
             20                  25                  30

Ile Ala Pro Lys Arg Tyr Lys Ala Asn Tyr Cys Ser Gly Glu Cys Glu
         35                  40                  45

Phe Asn Asn Phe Thr Val Ser Phe Trp Leu Arg Val Pro Lys Val Ser
     50                  55                  60

Ala Ser His Leu Glu Ala Gly Pro Cys Cys Thr Pro Thr Lys Met Ser
 65                  70                  75                  80

Pro Ile Asn Met Leu Tyr Phe Asn Gly Lys Glu Gln Ile Ile Tyr Gly
                 85                  90                  95

Lys Ile Pro Ala Met Val Val Asp Arg Cys Gly Cys Ser
            100                 105


<210> SEQ ID NO 20
<211> LENGTH: 109
<212> TYPE: PRT
<213> ORGANISM: Artificial sequence
<220> FEATURE:
<221> NAME/KEY: MUTAGEN
<222> LOCATION: (79)..(99)
<223> OTHER INFORMATION: Tetanus toxoid P30 epitope (SEQ ID NO: 14)
<220> FEATURE:
<221> NAME/KEY: SIMILAR
<222> LOCATION: (1)..(78)
<223> OTHER INFORMATION: Identical to residues 267-345 in SEQ ID NO: 1
<220> FEATURE:
<221> NAME/KEY: SIMILAR
<222> LOCATION: (100)..(109)
<223> OTHER INFORMATION: Identical to residues 366-375 in SEQ ID NO: 1
<220> FEATURE:
<221> NAME/KEY: SITE
<222> LOCATION: (73)
<223> OTHER INFORMATION: Cys or Ser
<220> FEATURE:
<221> NAME/KEY: SITE
<222> LOCATION: (90)..(91)
<223> OTHER INFORMATION: Lys Glu or Glu Gly
```

-continued

<400> SEQUENCE: 20

```
Asp Phe Gly Leu Asp Cys Asp Glu His Ser Thr Glu Ser Arg Cys Cys
  1               5                  10                  15

Arg Tyr Pro Leu Thr Val Asp Phe Glu Ala Phe Gly Trp Asp Trp Ile
             20                  25                  30

Ile Ala Pro Lys Arg Tyr Lys Ala Asn Tyr Cys Ser Gly Glu Cys Glu
         35                  40                  45

Phe Val Phe Leu Gln Lys Tyr Pro His Thr His Leu Val His Gln Ala
     50                  55                  60

Asn Pro Arg Gly Ser Ala Gly Pro Cys Cys Thr Pro Thr Lys Phe Asn
 65                  70                  75                  80

Asn Phe Thr Val Ser Phe Trp Leu Arg Val Pro Lys Val Ser Ala Ser
                 85                  90                  95

His Leu Glu Ala Met Val Val Asp Arg Cys Gly Cys Ser
            100                 105
```

<210> SEQ ID NO 21
<211> LENGTH: 109
<212> TYPE: PRT
<213> ORGANISM: Artificial sequence
<220> FEATURE:
<221> NAME/KEY: MUTAGEN
<222> LOCATION: (84)..(104)
<223> OTHER INFORMATION: Tetanus toxoid P30 epitope (SEQ ID NO: 14)
<220> FEATURE:
<221> NAME/KEY: SIMILAR
<222> LOCATION: (1)..(83)
<223> OTHER INFORMATION: Identical to residues 267-349 in SEQ ID NO: 1
<220> FEATURE:
<221> NAME/KEY: SIMILAR
<222> LOCATION: (105)..(109)
<223> OTHER INFORMATION: Identical to residues 371-375 in SEQ ID NO: 1
<220> FEATURE:
<221> NAME/KEY: SITE
<222> LOCATION: (73)
<223> OTHER INFORMATION: Cys or Ser
<220> FEATURE:
<221> NAME/KEY: SITE
<222> LOCATION: (90)..(91)
<223> OTHER INFORMATION: Lys Glu or Glu Gly

<400> SEQUENCE: 21

```
Asp Phe Gly Leu Asp Cys Asp Glu His Ser Thr Glu Ser Arg Cys Cys
  1               5                  10                  15

Arg Tyr Pro Leu Thr Val Asp Phe Glu Ala Phe Gly Trp Asp Trp Ile
             20                  25                  30

Ile Ala Pro Lys Arg Tyr Lys Ala Asn Tyr Cys Ser Gly Glu Cys Glu
         35                  40                  45

Phe Val Phe Leu Gln Lys Tyr Pro His Thr His Leu Val His Gln Ala
     50                  55                  60

Asn Pro Arg Gly Ser Ala Gly Pro Cys Cys Thr Pro Thr Lys Met Ser
 65                  70                  75                  80

Pro Ile Asn Phe Asn Asn Phe Thr Val Ser Phe Trp Leu Arg Val Pro
                 85                  90                  95

Lys Val Ser Ala Ser His Leu Glu Arg Cys Gly Cys Ser
            100                 105
```

<210> SEQ ID NO 22
<211> LENGTH: 254
<212> TYPE: PRT
<213> ORGANISM: Artificial sequence
<220> FEATURE:
<221> NAME/KEY: SIMILAR -continued

```
<222> LOCATION: (110)..(124)
<223> OTHER INFORMATION: Tetanus toxoid P2 epitope (SEQ ID NO: 13)
<220> FEATURE:
<221> NAME/KEY: SIMILAR
<222> LOCATION: (125)..(145)
<223> OTHER INFORMATION: Diptheria toxoid P30 epitope (SEQ ID NO: 14)
<220> FEATURE:
<221> NAME/KEY: SIMILAR
<222> LOCATION: (1)..(109)
<223> OTHER INFORMATION: 109 C-terminal residues of human and bovine
      GDF-8 (residues 267-375 in SEQ ID NO: 1)
<220> FEATURE:
<221> NAME/KEY: SIMILAR
<222> LOCATION: (146)..(254)
<223> OTHER INFORMATION: 109 C-terminal residues of human and bovine
      GDF-8 (residues 267-375 in SEQ ID NO: 1
<220> FEATURE:
<221> NAME/KEY: SITE
<222> LOCATION: (90)..(91)
<223> OTHER INFORMATION: Lys Glu or Glu Gly
<220> FEATURE:
<221> NAME/KEY: SITE
<222> LOCATION: (235)..(236)
<223> OTHER INFORMATION: Identical to (90)..(91)

<400> SEQUENCE: 22

Asp Phe Gly Leu Asp Cys Asp Glu His Ser Thr Glu Ser Arg Cys Cys
  1               5                  10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
     50                  55                  60

Asn Pro Arg Gly Ser Ala Gly Pro Cys Cys Thr Pro Thr Lys Met Ser
 65                  70                  75                  80

Pro Ile Asn Met Leu Tyr Phe Asn Gly Lys Glu Gln Ile Ile Tyr Gly
                 85                  90                  95

Lys Ile Pro Ala Met Val Val Asp Arg Cys Gly Cys Ser Gln Tyr Ile
            100                 105                 110

Lys Ala Asn Ser Lys Phe Ile Gly Ile Thr Glu Leu Phe Asn Asn Phe
        115                 120                 125

Thr Val Ser Phe Trp Leu Arg Val Pro Lys Val Ser Ala Ser His Leu
    130                 135                 140

Glu Asp Phe Gly Leu Asp Cys Asp Glu His Ser Thr Glu Ser Arg Cys
145                 150                 155                 160

Cys Arg Tyr Pro Leu Thr Val Asp Phe Glu Ala Phe Gly Trp Asp Trp
                165                 170                 175

Ile Ile Ala Pro Lys Arg Tyr Lys Ala Asn Tyr Cys Ser Gly Glu Cys
            180                 185                 190

Glu Phe Val Phe Leu Gln Lys Tyr Pro His Thr His Leu Val His Gln
        195                 200                 205

Ala Asn Pro Arg Gly Ser Ala Gly Pro Cys Cys Thr Pro Thr Lys Met
    210                 215                 220

Ser Pro Ile Asn Met Leu Tyr Phe Asn Gly Lys Glu Gln Ile Ile Tyr
225                 230                 235                 240

Gly Lys Ile Pro Ala Met Val Val Asp Arg Cys Gly Cys Ser
                245                 250


<210> SEQ ID NO 23
<211> LENGTH: 160
<212> TYPE: PRT
```

-continued

```
<213> ORGANISM: Artificial sequence
<220> FEATURE:
<221> NAME/KEY: MUTAGEN
<222> LOCATION: (16)..(36)
<223> OTHER INFORMATION: Tetanus toxoid P30 epitope (SEQ ID NO: 14)
<220> FEATURE:
<221> NAME/KEY: MUTAGEN
<222> LOCATION: (37)..(51)
<223> OTHER INFORMATION: Tetanus toxoid P2 epitope (SEQ ID NO: 13)
<220> FEATURE:
<221> NAME/KEY: SIMILAR
<222> LOCATION: (1)..(15)
<223> OTHER INFORMATION: Identical to residues 216-230 of SEQ ID NO: 1
<220> FEATURE:
<221> NAME/KEY: SIMILAR
<222> LOCATION: (52)..(160)
<223> OTHER INFORMATION: Identical to residues 267-375 of SEQ ID NO: 1
<220> FEATURE:
<221> NAME/KEY: SITE
<222> LOCATION: (124)
<223> OTHER INFORMATION: Cys or Ser
<220> FEATURE:
<221> NAME/KEY: SITE
<222> LOCATION: (141)..(142)
<223> OTHER INFORMATION: Lys Glu or Glu Gly

<400> SEQUENCE: 23

Leu Lys Gln Pro Glu Ser Asn Leu Gly Ile Glu Ile Lys Ala Leu Phe
  1               5                  10                  15

Asn Asn Phe Thr Val Ser Phe Trp Leu Arg Val Pro Lys Val Ser Ala
             20                  25                  30

Ser His Leu Glu Gln Tyr Ile Lys Ala Asn Ser Lys Phe Ile Gly Ile
        35                  40                  45

Thr Glu Leu Asp Phe Gly Leu Asp Cys Asp Glu His Ser Thr Glu Ser
     50                  55                  60

Arg Cys Cys Arg Tyr Pro Leu Thr Val Asp Phe Glu Ala Phe Gly Trp
 65                  70                  75                  80

Asp Trp Ile Ile Ala Pro Lys Arg Tyr Lys Ala Asn Tyr Cys Ser Gly
                 85                  90                  95

Glu Cys Glu Phe Val Phe Leu Gln Lys Tyr Pro His Thr His Leu Val
            100                 105                 110

His Gln Ala Asn Pro Arg Gly Ser Ala Gly Pro Cys Cys Thr Pro Thr
        115                 120                 125

Lys Met Ser Pro Ile Asn Met Leu Tyr Phe Asn Gly Lys Glu Gln Ile
    130                 135                 140

Ile Tyr Gly Lys Ile Pro Ala Met Val Val Asp Arg Cys Gly Cys Ser
145                 150                 155                 160


<210> SEQ ID NO 24
<211> LENGTH: 13
<212> TYPE: PRT
<213> ORGANISM: Unknown
<220> FEATURE:
<223> OTHER INFORMATION: PADRE Peptide

<400> SEQUENCE: 24

Ala Lys Phe Val Ala Ala Trp Thr Leu Lys Ala Ala Ala
  1               5                  10
```